US010154838B2

(12) United States Patent
Solem

(10) Patent No.: US 10,154,838 B2
(45) Date of Patent: *Dec. 18, 2018

(54) SUTURE AND METHOD FOR REPAIRING A HEART

(71) Applicant: Edwards Lifesciences Corporation, Irvine, CA (US)

(72) Inventor: Jan Otto Solem, Bjarred (SE)

(73) Assignee: Edwards Lifesciences Corporation, Irvine, CA (US)

( * ) Notice: Subject to any disclaimer, the term of this patent is extended or adjusted under 35 U.S.C. 154(b) by 156 days.

This patent is subject to a terminal disclaimer.

(21) Appl. No.: 15/402,603

(22) Filed: Jan. 10, 2017

(65) Prior Publication Data
US 2017/0119368 A1 May 4, 2017

Related U.S. Application Data

(60) Continuation of application No. 15/232,274, filed on Aug. 9, 2016, now Pat. No. 9,572,667, which is a
(Continued)

(51) Int. Cl.
A61B 17/04 (2006.01)
A61F 2/00 (2006.01)
(Continued)

(52) U.S. Cl.
CPC .... A61B 17/0401 (2013.01); A61B 17/00234 (2013.01); A61F 2/0077 (2013.01);
(Continued)

(58) Field of Classification Search
CPC .......... A61B 17/00234; A61B 17/0401; A61B 17/0487; A61B 17/06166;
(Continued)

(56) References Cited

U.S. PATENT DOCUMENTS 3,394,704 A 7/1968 Edmund
6,136,010 A 10/2000 Modesitt et al.
(Continued)

FOREIGN PATENT DOCUMENTS

EP 1600121 A1 11/2005
WO 0230335 A2 4/2002
(Continued)

OTHER PUBLICATIONS

International Search Report, dated Jul. 7, 2008.

Primary Examiner — Jonathan Miles
Assistant Examiner — Majid Jamialahmadi
(74) Attorney, Agent, or Firm — Michael Crapenhoft

(57) ABSTRACT

Devices and methods for treating or repairing a heart are disclosed. The device includes at least one radially expandable tissue-engaging element, an elongate member (e.g., suture) coupled to the expandable element, and a locking mechanism (e.g., locking clip, suture knot). The expandable element may be anchored to heart tissue within the heart, such as in the left ventricle, with the elongate member extending from the expandable element and across a heart chamber to a second location such as the heart apex where the elongate member is held by the locking mechanism.

18 Claims, 34 Drawing Sheets

Related U.S. Application Data division of application No. 13/662,128, filed on Oct. 26, 2012, which is a division of application No. 12/031,490, filed on Feb. 14, 2008.

(60) Provisional application No. 60/889,921, filed on Feb. 14, 2007.

(51) Int. Cl.

| | | |
|---|---|---|
| *A61F 2/24* | (2006.01) | |
| *A61B 17/00* | (2006.01) | |
| *A61B 17/06* | (2006.01) | |
| *A61B 17/30* | (2006.01) | |

(52) U.S. Cl.
CPC .............. *A61F 2/24* (2013.01); *A61F 2/2457* (2013.01); *A61F 2/2466* (2013.01); *A61F 2/2487* (2013.01); *A61B 17/0467* (2013.01); *A61B 17/0487* (2013.01); *A61B 17/06166* (2013.01); *A61B 2017/003* (2013.01); *A61B 2017/00004* (2013.01); *A61B 2017/00243* (2013.01); *A61B 2017/00876* (2013.01); *A61B 2017/0409* (2013.01); *A61B 2017/0417* (2013.01); *A61B 2017/0427* (2013.01); *A61B 2017/0464* (2013.01); *A61B 2017/06057* (2013.01); *A61B 2017/306* (2013.01); *A61F 2002/0086* (2013.01); *A61F 2210/0004* (2013.01); *A61F 2210/009* (2013.01)

(58) Field of Classification Search
CPC .. A61B 2017/00243; A61B 2017/0409; A61B 2017/0427; A61F 2/2457; A61F 2/2466; A61F 2/2487
See application file for complete search history.

(56) References Cited

U.S. PATENT DOCUMENTS

| | | | |
|---|---|---|---|
| 6,165,183 A | 12/2000 | Kuehn et al. | |
| 6,210,432 B1 | 4/2001 | Solem et al. | |
| 6,332,863 B1 | 12/2001 | Schweich, Jr. et al. | |
| 6,537,314 B2 | 3/2003 | Langberg et al. | |
| 6,626,930 B1 | 9/2003 | Allen et al. | |
| 6,997,951 B2 | 2/2006 | Solem et al. | |
| 7,011,669 B2 | 3/2006 | Kimblad | |
| 7,044,967 B1 | 5/2006 | Solem et al. | |
| 7,083,628 B2 | 8/2006 | Bachman | |
| 7,094,244 B2 | 8/2006 | Schreck | |
| 7,192,442 B2 | 3/2007 | Solem et al. | |
| 7,192,443 B2 | 3/2007 | Solem et al. | |
| 7,381,210 B2 | 6/2008 | Zarbatany et al. | |
| 7,431,692 B2 | 10/2008 | Zollinger et al. | |
| 7,500,989 B2 | 3/2009 | Solem et al. | |
| 7,507,252 B2 | 3/2009 | Lashinski et al. | |
| 9,572,667 B2 * | 2/2017 | Solem ................... | A61F 2/2457 |
| 2003/0069628 A1 | 4/2003 | Solem | |
| 2003/0069636 A1 | 4/2003 | Solem et al. | |
| 2003/0120341 A1 * | 6/2003 | Shennib ............... | A61B 5/0215 |
| | | | 623/2.12 |
| 2004/0102840 A1 | 5/2004 | Solem et al. | |
| 2005/0043792 A1 | 2/2005 | Solem et al. | |
| 2005/0177180 A1 * | 8/2005 | Kaganov .......... | A61B 17/00234 |
| | | | 606/151 |
| 2005/0177228 A1 | 8/2005 | Solem et al. | |
| 2005/0228422 A1 | 10/2005 | Machold et al. | |
| 2006/0004248 A1 | 1/2006 | Kute et al. | |
| 2006/0058871 A1 | 3/2006 | Zakay et al. | |
| 2006/0116756 A1 | 6/2006 | Solem et al. | |
| 2006/0207607 A1 | 9/2006 | Hirotsuka et al. | |
| 2006/0241745 A1 | 10/2006 | Solem | |
| 2007/0061010 A1 | 3/2007 | Hauser et al. | |
| 2007/0073391 A1 | 3/2007 | Bourang et al. | |
| 2007/0270943 A1 | 11/2007 | Solem | |
| 2007/0282429 A1 | 12/2007 | Hauser et al. | |
| 2009/0054724 A1 | 2/2009 | Hauser et al. | |

FOREIGN PATENT DOCUMENTS

| | | |
|---|---|---|
| WO | 2004112658 A1 | 12/2004 |
| WO | 2005102181 A1 | 11/2005 |
| WO | 2006039223 A2 | 4/2006 |
| WO | 2006105008 A1 | 10/2006 |
| WO | 2006111391 A1 | 10/2006 |

* cited by examiner

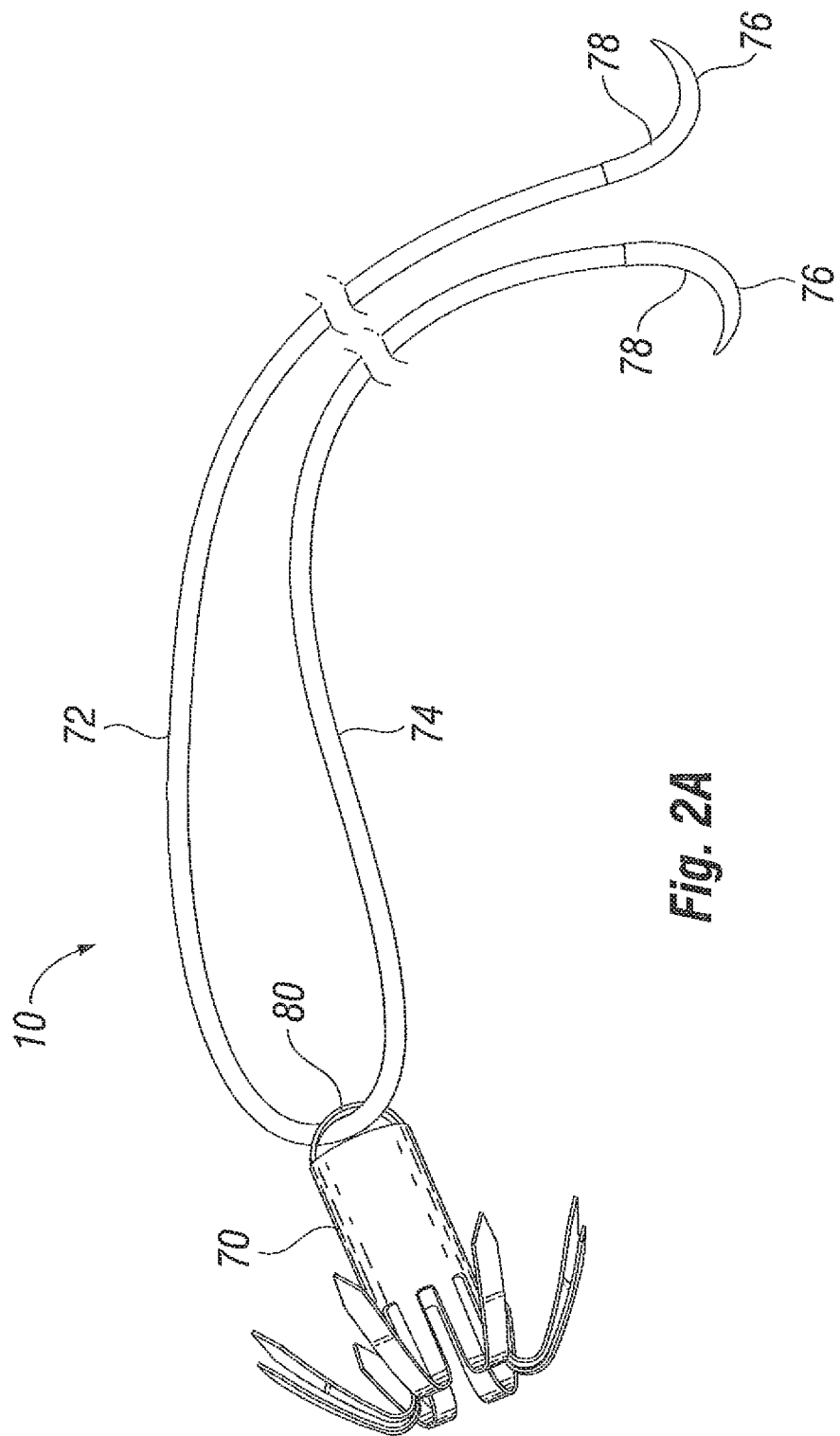

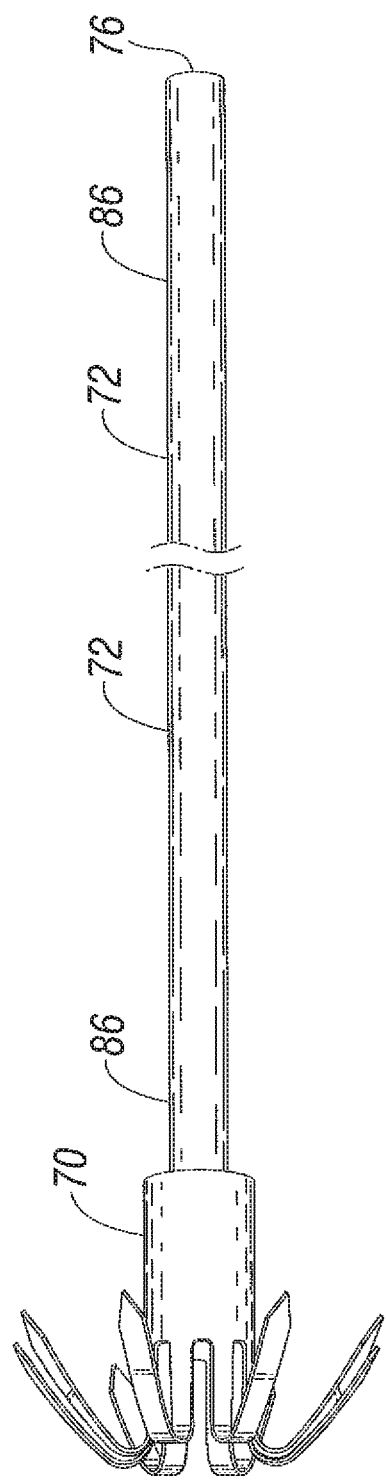

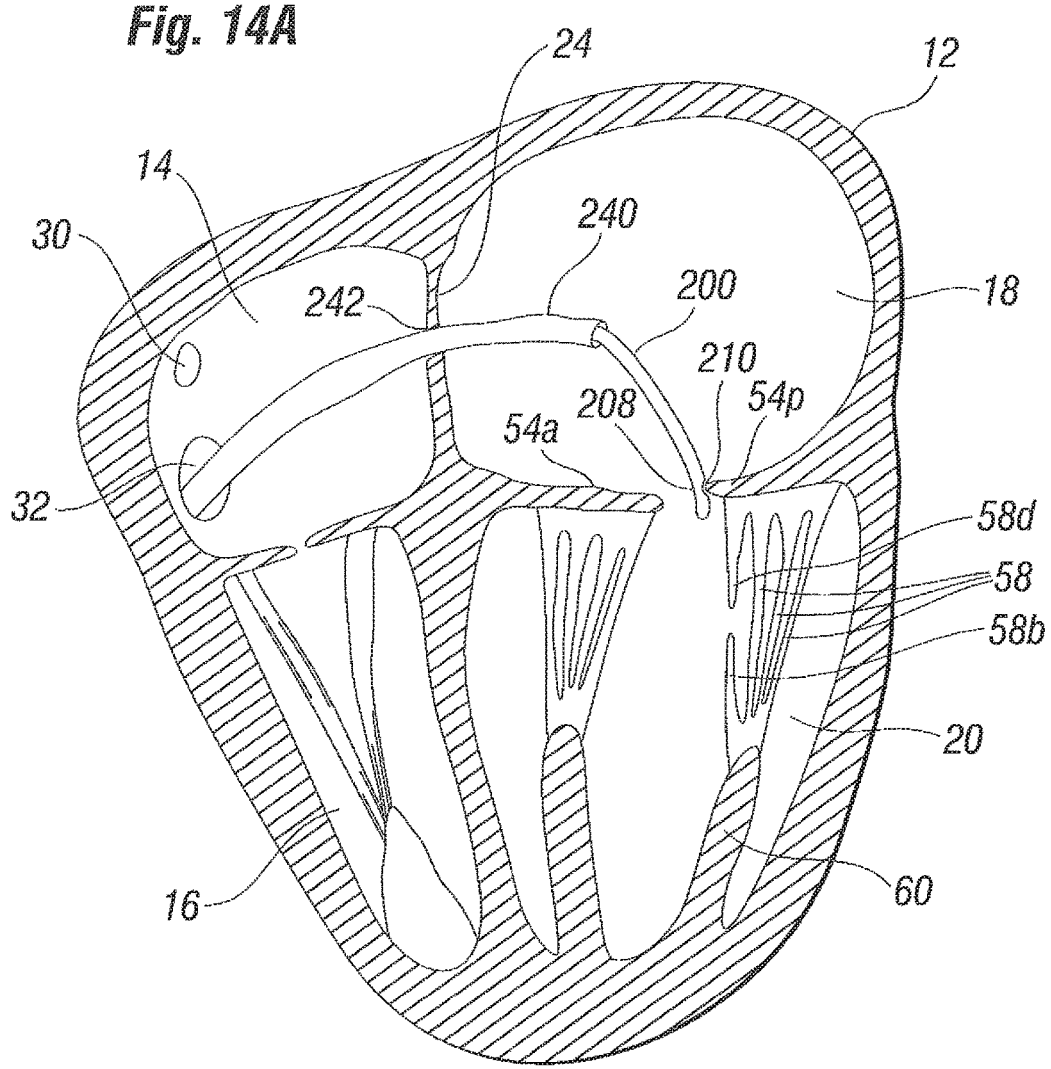

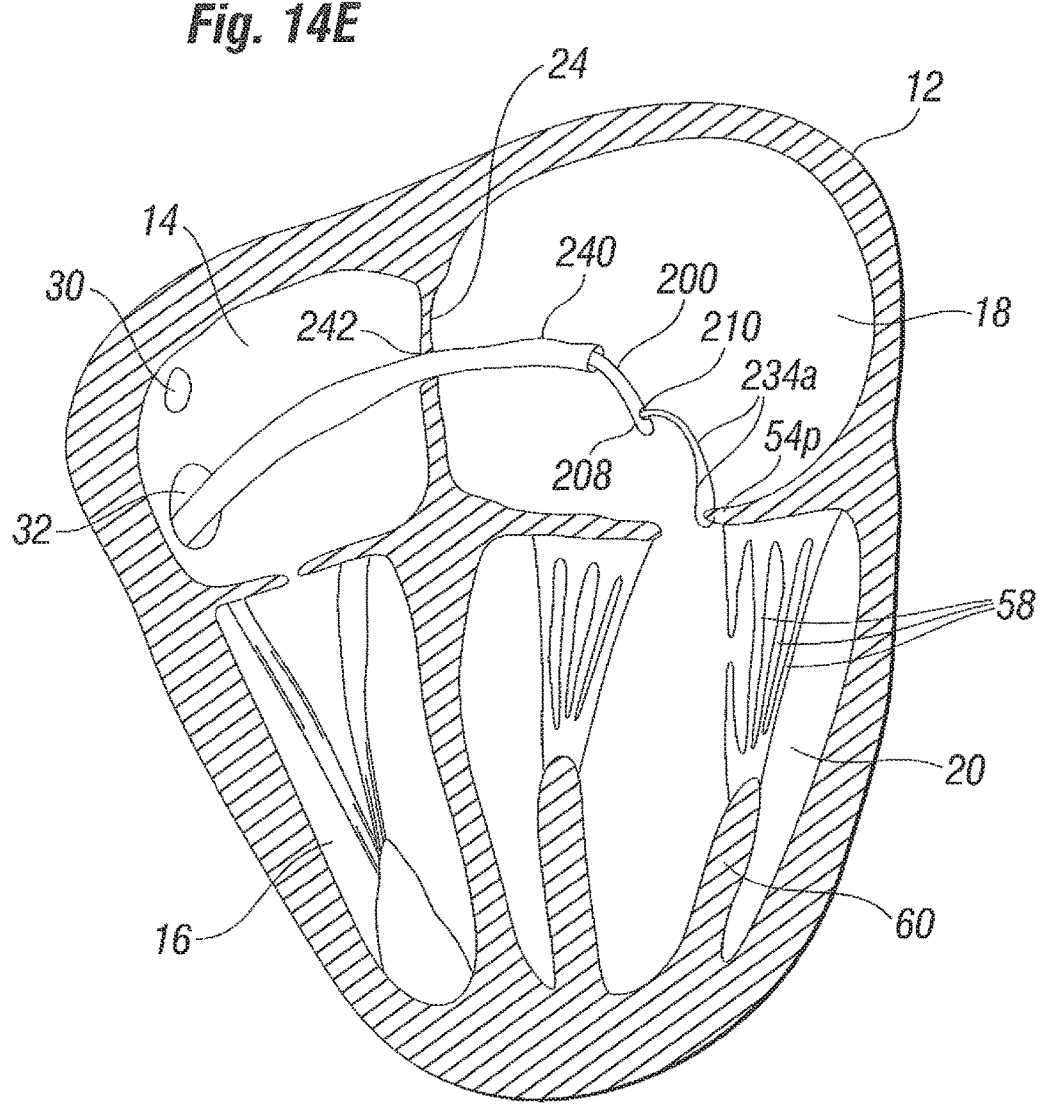

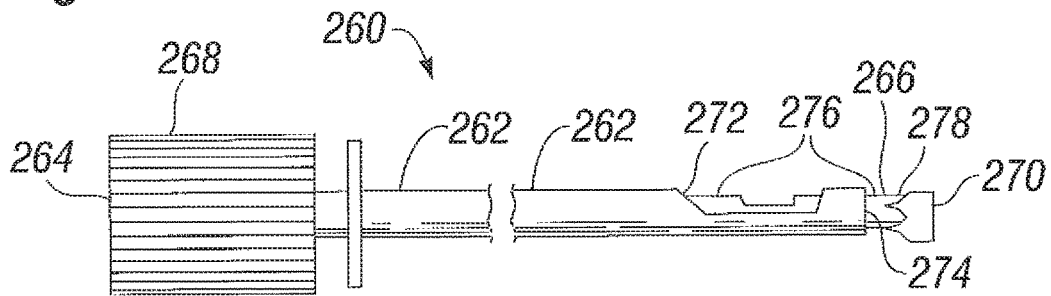
Fig. 16A
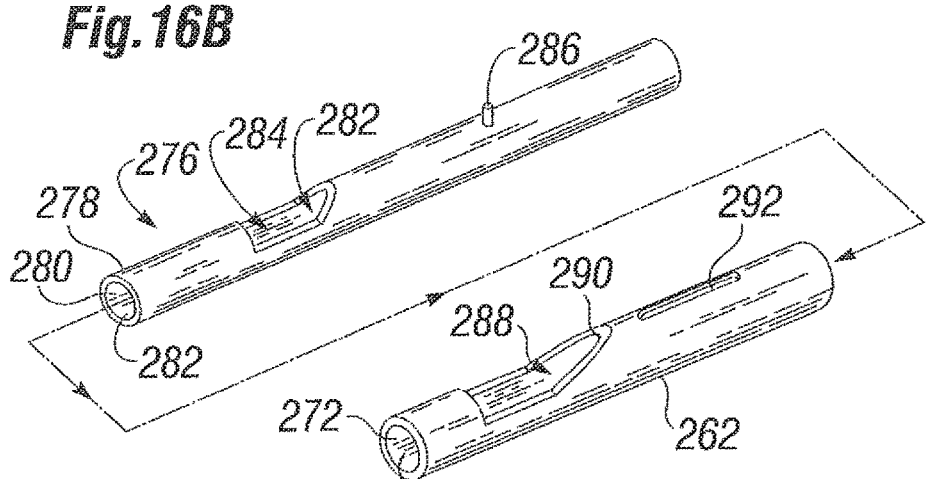
Fig. 16B
Fig. 16C
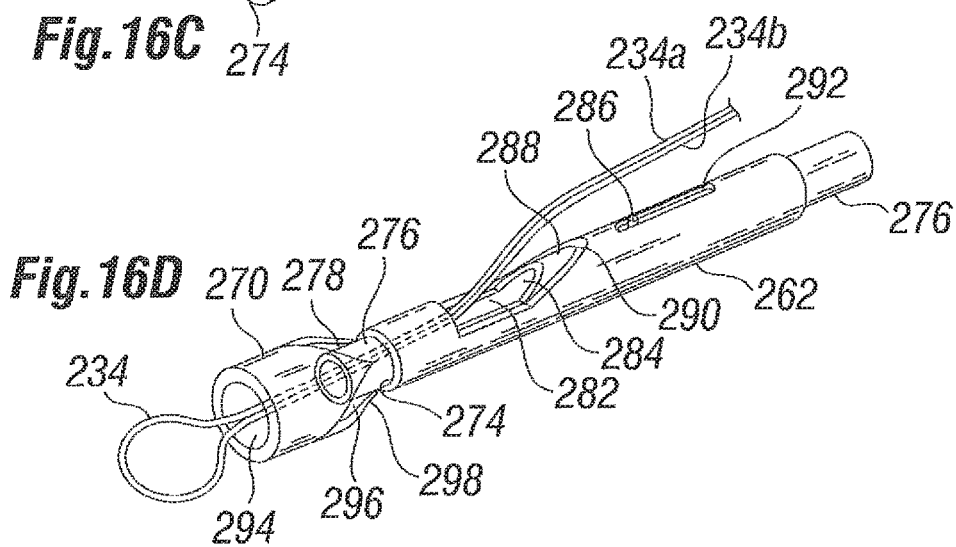
Fig. 16D

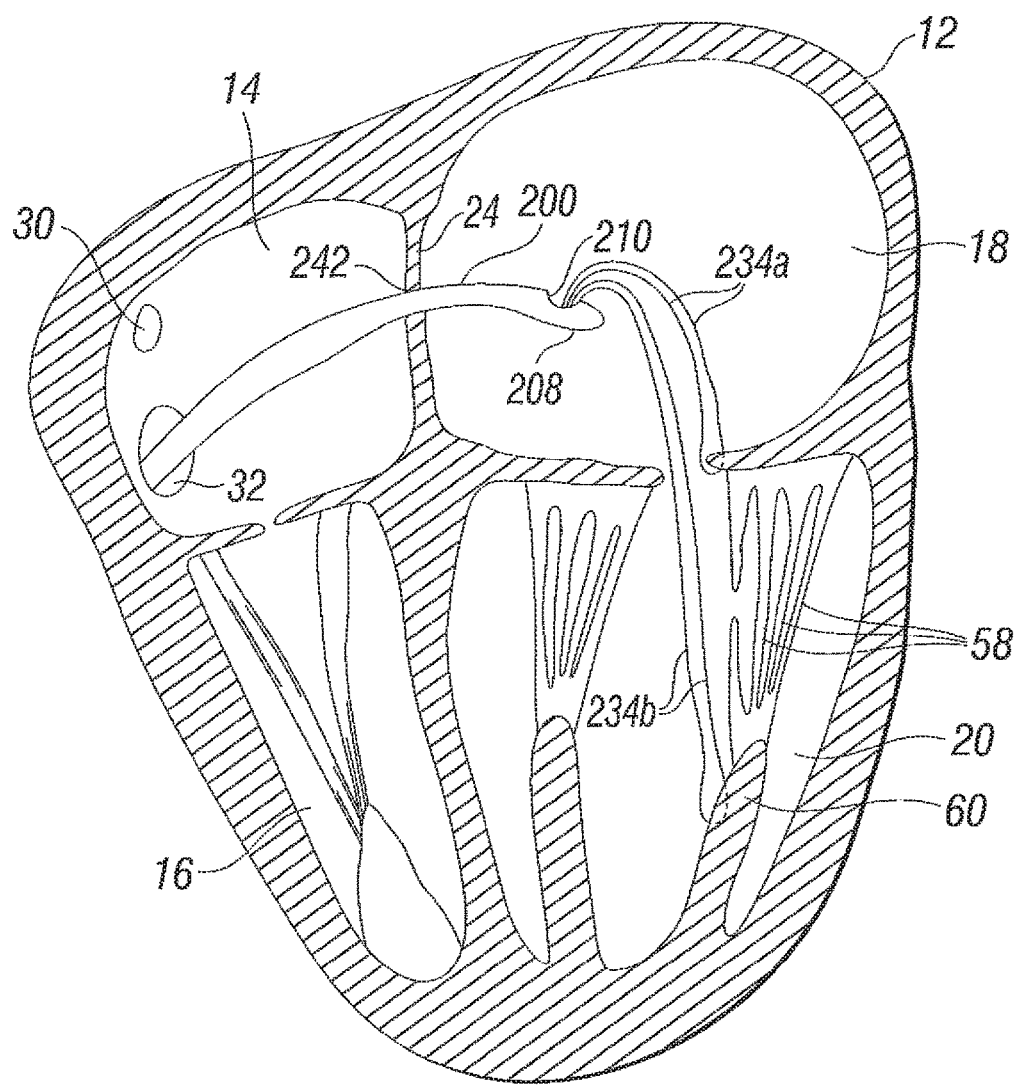

SUTURE AND METHOD FOR REPAIRING A HEART

RELATED APPLICATIONS

The present application is a continuation of U.S. utility application Ser. No. 15/232,274, filed Aug. 9, 2016, which is a division of co-pending U.S. utility patent application Ser. No. 13/662,128, filed Oct. 26, 2012 and entitled "Suture and Method for Repairing a Heart," which is a division of co-pending U.S. utility patent application Ser. No. 12/031,490, filed Feb. 14, 2008 and entitled "Suture and Method for Repairing a Heart," which claims priority from U.S. provisional patent application Ser. No. 60/889,921, filed on Feb. 14, 2007 and entitled "Suture and Method for Repairing a Heart," the entire contents of each of which are expressly incorporated herein in their entirety.

FIELD OF THE INVENTION

The present invention relates generally to medical devices, and more particularly, to implantable medical devices for treating diseases, disorders, and malformations of a heart

BACKGROUND OF THE INVENTION

The function of the heart may be seriously impaired if any of the heart valves is not functioning properly. The heart valves may lose their ability to close properly due to disease or defects, such as (for example) by a mitral or tricuspid valve leaflet becoming partially or completely detached from a papillary muscle (e.g., by ruptured chordae tendinae) thereby resulting in prolapsing of the leaflet. The inability of the heart valve to close will cause a leak backwards, commonly referred to as regurgitation, through the valve. On the left side of the heart, regurgitation through the mitral valve may seriously impair the function of the heart 1 since a portion of the heart stroke volume of blood will return from the left ventricle to the left atrium instead of passing through the aortic valve to the organs of the body. Accordingly, the damaged heart is required to work much harder to maintain adequate circulation, a condition that inevitably ends in heart enlargement and/or heart failure.

Repairing heart structures by means of surgery often involves the use of needle and thread for attaching tissue portions together or for attaching a prosthetic implant to tissue. A traditional surgical suture typically has a needle attached to one or both ends of a thread. In a common method for attaching a suture directly to tissue (i.e., when not directly attaching tissue to tissue or tissue to implants), one needle is passed through the tissue one or several times and advanced to about the middle of the thread. The thread may or may not be knotted at this point to prevent the thread from moving slidingly through the tissue. Whether knotted or not, the end result is that the thread is attached to the tissue.

While performing heart surgery, the above technique is often used in chordae tendinae replacement. A first end of a suture thread is attached to a papillary muscle inside the left ventricle of a heart. The appropriate length of the thread is determined, and the other end of the suture thread is stitched through one or more of the leaflets of the mitral valve for creating artificial chordae tendinae. This procedure can be performed for treating a regurgitant mitral valve when the reason for the regurgitation (i.e., leak) is prolapse of a mitral valve leaflet into the left atrium. However, attaching a thread (i.e., suture) to the papillary muscle can be cumbersome due to difficulties in accessing the surgical site, including limitations in physical and visual access. The limited visual access results from the relatively narrow space between the leaflets of a mitral valve. Furthermore, access to the desired portion of the heart can be difficult while performing conventional open-heart surgery (i.e., with a sternal split). Further difficulties can arise as a result of the difficult angles at which the instruments are held.

Due to the shortcomings associated with existing medical procedures, the attachment of artificial chordae can be time consuming and may often be inaccurate. Accordingly, a need exists for improved devices and methods for creating artificial chordae. To reduce the trauma to the patient, it is desirable that the devices and methods be adapted for use in a percutaneous or minimally-invasive procedure. The present invention addresses this need.

SUMMARY OF THE INVENTION

Embodiments of the present invention provide devices and methods for securely attaching a thread to tissue without the need for conventional suturing, thereby eliminating the need for surgical instruments such as needle holders and forceps. Some embodiments are adapted for attaching thread to heart wall tissue; however, the features of the invention are also applicable to a wide variety of other medical procedures wherein it is desirable to securely anchor a suture thread or other structure to a portion of tissue without using a needle and forceps.

Embodiments of the invention include new devices and methods for creating artificial chordae and for repairing various other heart defects without suturing. In one variation, embodiments may be used to reduce dilation of a heart wall, such as in the left ventricle. In some embodiments of methods of use, these treatments are performed in a percutaneous manner by means of catheter access.

In one aspect, a suture device for repairing a human heart comprises a thread, an anchor, and a delivery system. The anchor is configured to engage tissue, such as tissue of an inner wall of the heart. The thread is attached to the anchor at one end and configured to be attached (via conventional suture tying, clipping, or otherwise) to heart tissue (such as valve leaflet tissue) at another end. The delivery system is configured to deliver the anchor in a delivery configuration, and to deploy the anchor into tissue at a desired location (such as at or adjacent papillary muscles of the heart). In some embodiments, the anchor comprises memory materials (such as Nitinol) and/or is biased toward the deployed state so that the anchor is configured to expand from a delivered state to a deployed state when ejected from a distal end of a sheath on the delivery catheter.

In one arrangement, the anchor is configured for attachment at or adjacent papillary muscle tissue, and the thread is configured to be coupled to the anchor and attached to a leaflet for creating an artificial chordae tendinae. The delivery system includes a sheath or other structure for delivering the anchor in a collapsed condition to the desired deployment location.

In another embodiment, a method for repairing a human heart comprises gaining access to the inner portion of a human heart and deploying a suture anchor. A thread is then attached to tissue and coupled to the anchor. The thread may be foreshortened to a desired length and then locked in the foreshortened position. This method may be used for replacing chordae tendinae, for treating dilation of a left ventricle, or for other heart treatments.

In another embodiment, a method of treating mitral valve regurgitation comprises performing open heart surgery for gaining direct access to the left atrium and the mitral valve. An anchor is deployed along or adjacent to the papillary muscle, and an elongate member (e.g., thread) is attached at a first end to the anchor and at a second end to a mitral valve leaflet. If desired, the length of the elongate member may be adjusted to close a gap in the mitral valve, and the thread is then knotted or otherwise locked to the mitral valve leaflet to maintain the desired length.

In another embodiment, a method of treating an enlargement of a left ventricle of a heart comprises accessing the inside of a heart (e.g., through surgical incision) and deploying multiple anchor members at locations along the left ventricular muscular wall. Threads extending from the anchor members are connected to a lock. The threads are shortened to pull the anchors, and therefore the muscular wall, into closer proximity to the lock and to the other anchors. The threads are then locked in the shortened condition to maintain the anchors in closer proximity, thereby reducing the size of the left ventricle. In one embodiment, the lock is located within the left ventricle. In another embodiment, the lock is located within a different chamber of the heart, such as the right atrium or the right ventricle. In another embodiment, the lock is located outside of the heart, such as, for example, at or adjacent the apex of the heart.

In another aspect, a method of treating an enlargement of a ventricle of a heart comprises accessing the inside of a heart via a percutaneous or surgical incision, deploying anchors in the left ventricular muscular wall wherein suture threads extend from the anchors, and connecting the suture threads to a lock. The anchors are allowed to grow into the tissue such that they are securely attached to the heart wall. After sufficient time, the inside of the heart may be re-accessed by means of catheter-based technology for localizing the lock, and the suture threads are then foreshortened and locked.

BRIEF DESCRIPTION OF THE DRAWINGS

FIG. 2A illustrates a device comprising an anchor, an elongate member, and hooks according to an embodiment of the invention;

FIG. 3A depicts a device comprising an anchor and rod-like elongate member according to a further embodiment of the invention;

FIG. 14A is a front view of a heart, in cross section, with a suture deployment device advanced to a valve leaflet to deploy a suture according to an embodiment of the invention;

FIG. 14E is a front view of the heart, in cross section, from FIG. 14A with the suture deployment device having a suture secured to the valve leaflet;

FIG. 16A is a side view of a suture securing and cutting catheter for use in securing suture according to an embodiment of the invention;

FIGS. 16B-16D are exploded and assembled views of the distal portion of the suture securing and cutting catheter of FIG. 16A;

FIGS. 18A-18B are front views of a heart, in cross section, with a suture delivery catheter deploying suture through papillary muscle tissue according to an embodiment of the invention.

DETAILED DESCRIPTION OF PREFERRED EMBODIMENTS

Figure 1:
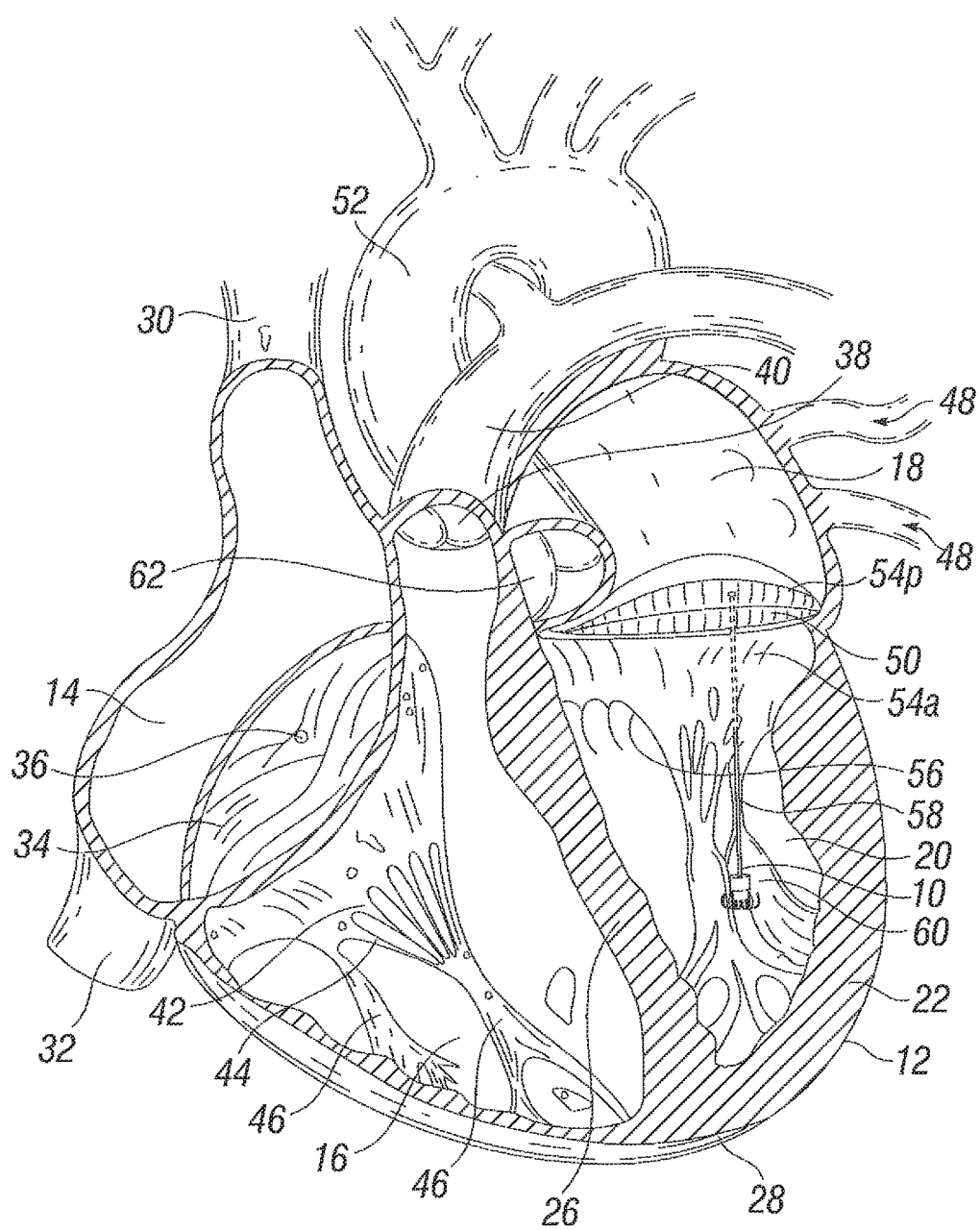
FIG. 1 shows a cross-sectional view of a human heart with a device according to an embodiment of the invention deployed therein.

With reference to FIG. 1, a device 10 according to the invention is depicted deployed within a heart 12. The heart 12 has four chambers, known as the right atrium 14, right ventricle 16, left atrium 18, and left ventricle 20. In the particular embodiment depicted, the device 10 is deployed in the left ventricle 20. The heart 12 has a muscular outer wall 22, with an interatrial septum 24 (not visible in FIG. 1) dividing the right atrium 14 and left atrium 18, and a muscular interventricular septum 26 dividing the right ventricle 16 and left ventricle 20. At the base of the heart 12 is the apex 28.

Blood flows through the superior vena cava 30 and the inferior vena cava 32 into the right atrium 14 of the heart 12. The tricuspid valve 34, which has three leaflets 36, controls blood flow between the right atrium 14 and the right ventricle 16. The tricuspid valve 34 is closed when blood is pumped out from the right ventricle 16 to the lungs. Thereafter, the tricuspid valve 34 is opened to refill the right ventricle 16 with blood from the right atrium 14. Lower portions and free edges 42 of leaflets 36 of the tricuspid valve 34 are connected via tricuspid chordae tendinae 44 to papillary muscles 46 in the right ventricle 16 for controlling the movements of the tricuspid valve 34. Blood from the right ventricle 18 is pumped through the pulmonary valve 38 to the pulmonary artery 40 which branches into arteries leading to the lungs.

After exiting the lungs, the newly-oxygenated blood flows through the pulmonary veins 48 and enters the left atrium 18 of the heart 12. The mitral valve 50 controls blood flow between the left atrium 18 and the left ventricle 20. The mitral valve 50 is closed during ventricular systole when blood is ejected from the left ventricle 20 into the aorta 52. Thereafter, the mitral valve 50 is opened to refill the left ventricle 20 with blood from the left atrium 18. The mitral valve has two leaflets (anterior leaflet 54a and posterior leaflet 54p), lower portions and free edges 56 of which are connected via mitral chordae tendinae 58 to papillary muscles 60 in the left ventricle 20 for controlling the movements of the mitral valve 50. Blood from the left ventricle 20 is pumped by power from the musculature of the heart wall 22 and the muscular interventricular septum 26 through the aortic valve 62 into the aorta 52 which branches into arteries leading to all parts of the body.

Figure 2B:
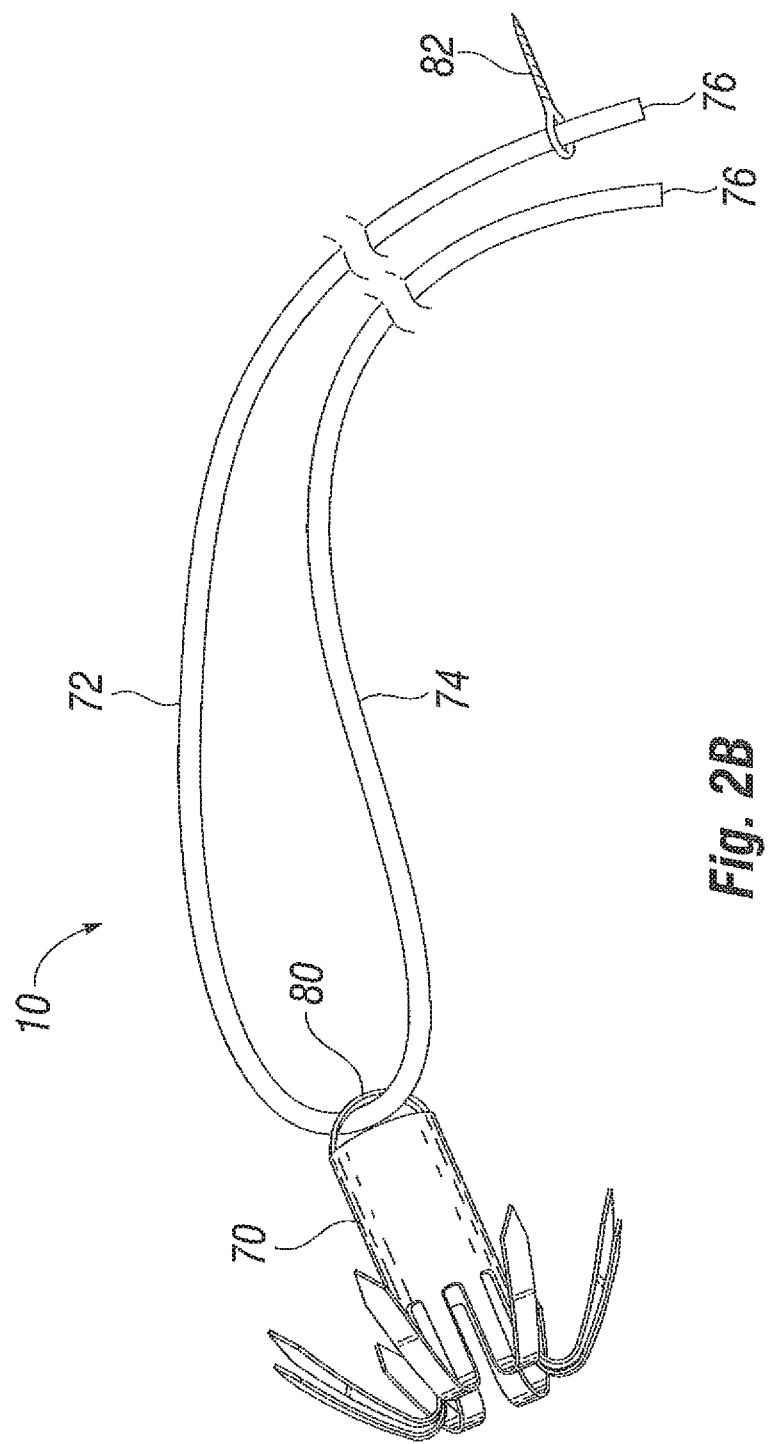
FIG. 2B illustrates a device comprising an anchor and an elongate member according to a further embodiment of the invention.
Figure 2C:
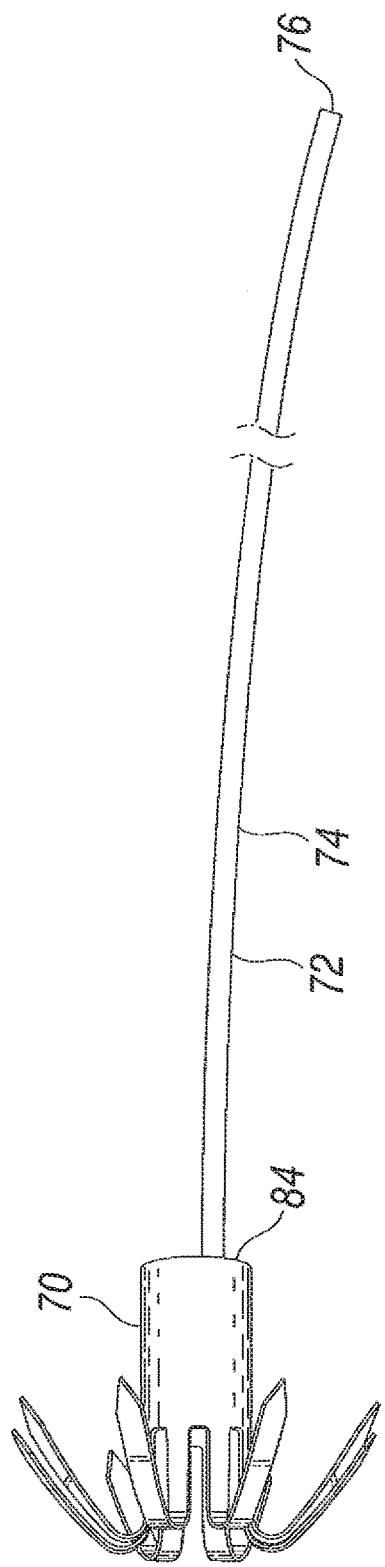
FIG. 2C illustrates a device comprising an anchor and an elongate member according to a further embodiment of the invention.

With reference now to FIGS. 2A-2C, for purposes of illustration, various embodiments of a treatment device 10 are shown. In the depicted embodiments, the treatment device 10 generally comprises an anchor 70 and an elongate member 72. The anchor 70 provides a mechanism for attaching the device to an inner heart wall or other deployment site without requiring the use of a suturing needle. The elongate member 72 is coupled to the anchor 70, such as by being looped therethrough or by other attachment thereto. In various applications, as will be described in more detail below, the elongate member 72 may be used for replacing a damaged or ruptured chordae tendinae or may be used for pulling a heart wall inward to reduce dilation of a heart wall. Features of anchors and elongate members according to various embodiments of the invention will be described in more detail below.

In the particular embodiment of FIG. 2A, the elongate member 72 comprises a thread 74 terminating at either end 76 in hooks or needles 78. The thread 74 passes through a hoop-like structure 80 on the anchor 70. The hooks or needles 78 on the free ends 76 of the thread 74 provide a physician or other user with the ability to penetrate tissue in the heart or elsewhere for fixing the free ends 76 of the elongate member 72.

Note that the thread 74 or other elongate member could terminate at free ends 76 without hooks, as depicted in FIG. 2B, which could be useful where one or more of the free ends 76 are to be passed through tissue using a detachable needle 82 or similar suturing device. Also, an elongate member 72, such as one or more threads 74, could be secured permanently or through other methods to the anchor 70, such as being secured directly and fixedly to the attachment point 84 depicted in FIG. 2C.

A thread portion of a device 10, such as the thread 74 depicted in FIGS. 2A-2C, may be formed of various materials, including PTFE (polytetrafluoroethylene, aka Goretex®), polypropylene (e.g. Prolene), or other suture materials such as Ti-crone or Ethibond. The hooks or needles could be attached to the threads according to known techniques, including techniques applied by suture material producers.

FIG. 3A depicts a further embodiment of the invention, wherein the elongate member 72 comprises a rod-like structure 86. In the particular embodiment depicted, the rod-like structure 86 is generally cylindrical, although other configurations are also possible. The rod-like structure 86 may be solid or hollow, depending on the particular configuration and application. The rod-like structure 86 may be generally rigid or may be generally flexible, or may be configured to be partially rigid but still have some flexibility so that it acts as a shock-absorbing structure when under compression.

Figure 3B:
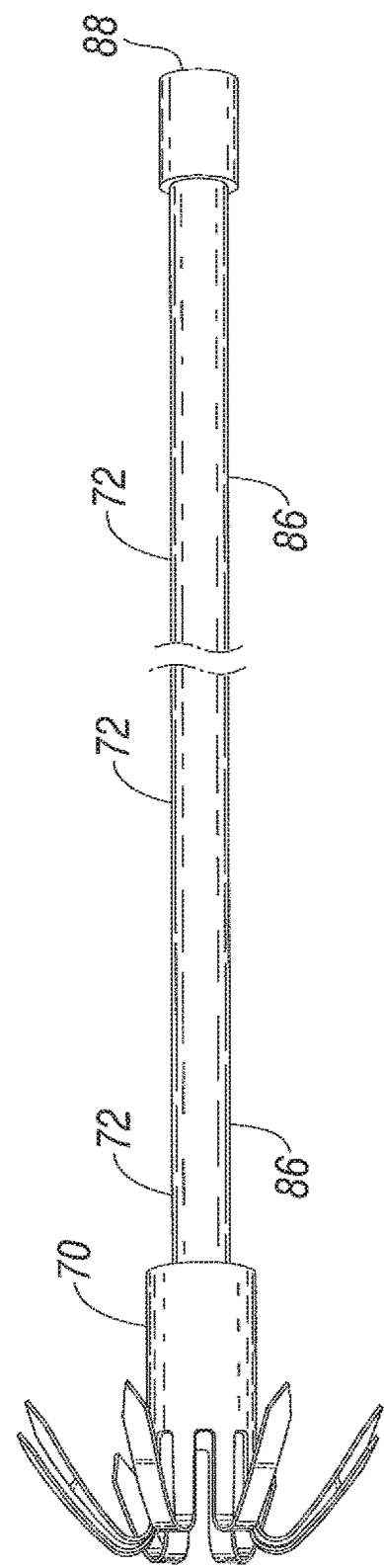
FIG. 3B depicts a device similar to that of FIG. 3A with a magnetic connector secured thereto according to an embodiment of the invention.

FIG. 3B depicts a further embodiment of the invention, wherein the elongate member 72 comprises a rod-like structure 86 having a magnet 88 secured at the free end 76. The magnet 88 might be used to pick up the elongate member 72 (in the form of a rod 76 or thread, etc.) at a later point of time, e.g., after the anchor has been deployed and grown solid into the tissue and the user desires to pull hard on the elongate member 72. The magnet 88 might be used to change an attached part of a device after a long time has passed, such as where the attached part is degenerated and has to be changed (e.g. a lock or a valve). The magnet 88 may also be used as a guiding aid, for instance when homing in and locking an elongate member (such as a thread) in a lock under open or percutaneous operations when the heart is beating and full of blood.

Figures 4A, 4B:
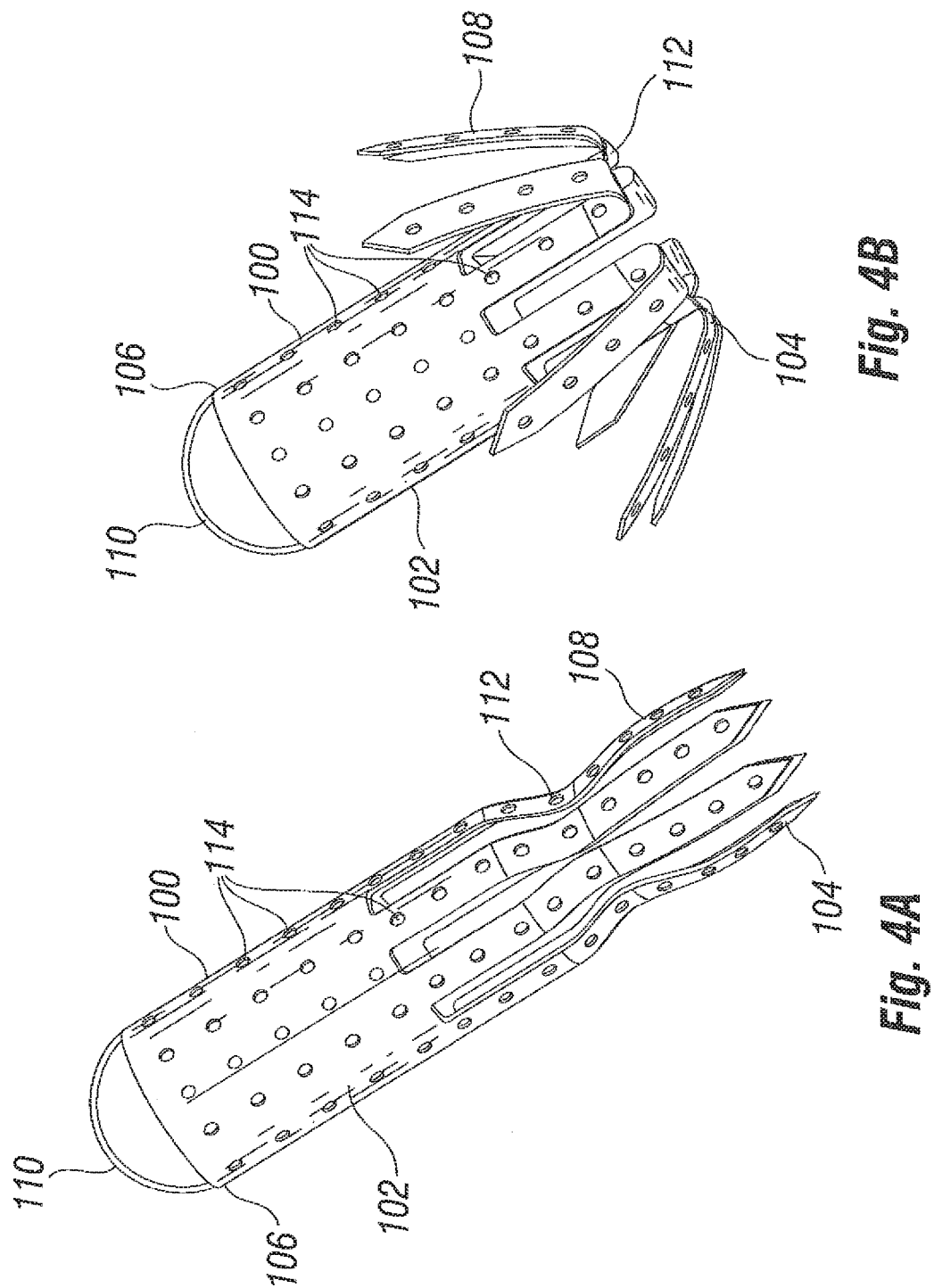
FIGS. 4A and 4B illustrate an expandable anchor, in unexpanded and expanded configurations, respectively, according to an embodiment of the invention.

With reference now to FIGS. 4A and 4B, for purposes of illustration a particular embodiment of an anchor portion 100 is described in more detail. The anchor portion 100 comprises a tubular body 102 having a distal end 104 and a proximal end 106, with a plurality of elongated prongs 108 located on the distal end 104 and a coupling member 110 located on the proximal end 106. In the illustrated embodiment, the coupling member 110 takes the form of a loop.

The elongated prongs 108 may be configured to self-expand from the compressed configuration of FIG. 4A to a "flowered" or expanded configuration of FIG. 4B. This expansion may be achieved with a self-curving area 112 that deflects the elongated prongs 108 radially outward from the center of the generally tubular body 102. The prongs 108 may be pointed and/or barbed to facilitate penetration of and engagement with the muscular wall of the heart.

The anchor portion 100 may be formed from various materials and/or combinations thereof. In one embodiment, the anchor portion 100 is formed from a single tube of shape memory material, such as, for example, Nitinol. During manufacture, the shape memory material (or other material forming the anchor portion 100) may be cut using a mechanical or laser cutting tool. After cutting the tube, the expanded or flowered shape can be imparted to the memory of the shape memory material with techniques known in the art (e.g. heat setting the shape). Note, however, that the anchor 100 is not limited to construction from Nitinol or other shape memory materials, and could be formed from any number of materials, including metals, plastics, composite structures, etc.

All or part of the surface of the anchor portion 100, including the prongs 108, may be configured to promote tissue growth onto and even into its surface. In one example this growth is achieved by providing a relatively rough and/or porous surface along the anchor portion 100. Another example is to have one or multiple holes 114 drilled through the anchor portion 100 and its prongs 108, allowing scar tissue fibrocytes to grow through these holes 114 and thereby add strength to the fixation. Additionally, biological coatings of the types known in the art can be included on the surface of the anchor portion 100 to promote healing and tissue growth.

Figures 5A, 5B:
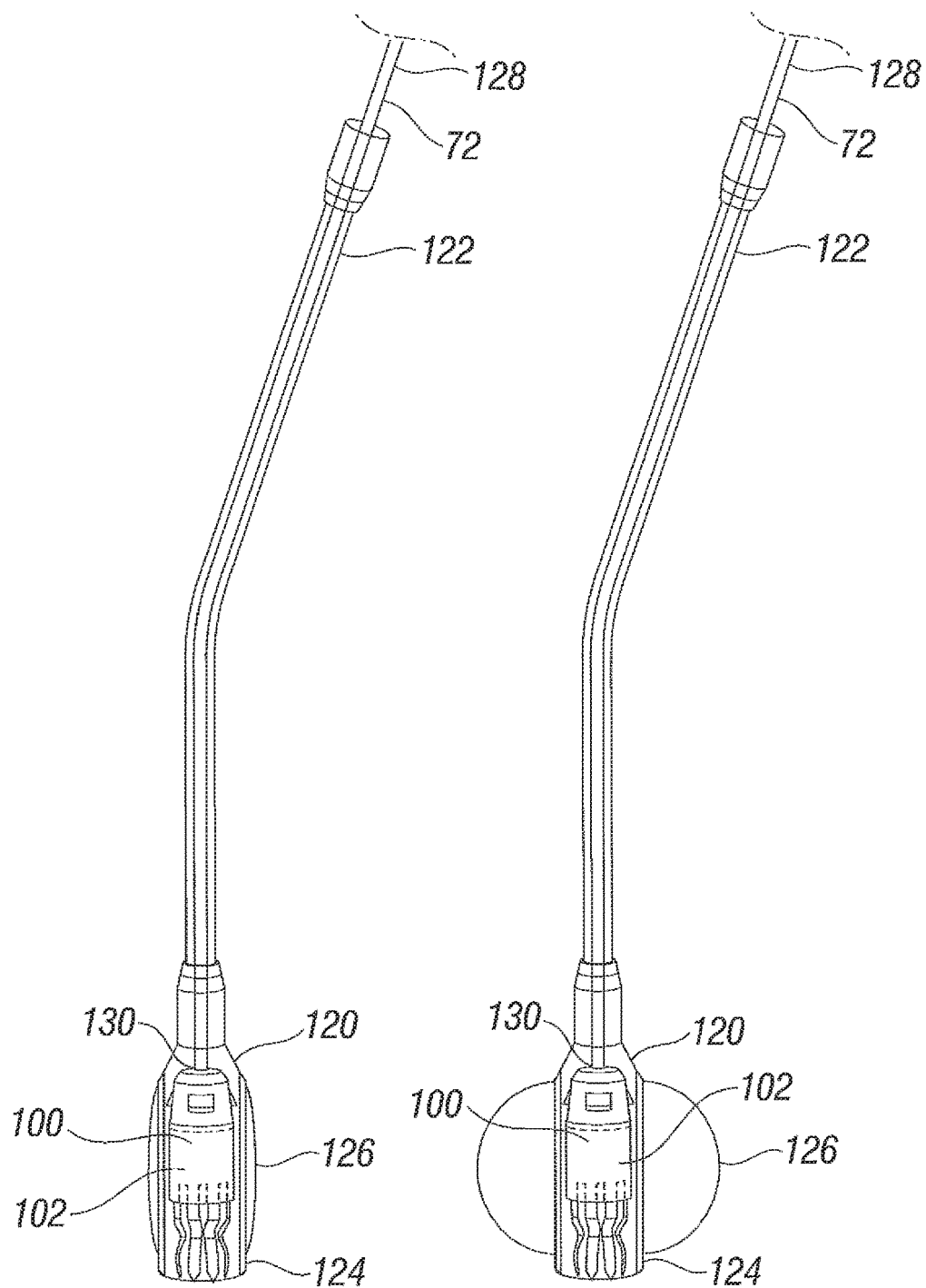
FIGS. 5A through 5D illustrate a method of delivering the device wherein a delivery system comprises a sheath for maintaining the anchor in the collapsed position during advancement according to an embodiment of the invention.

With reference to FIGS. 5A-5D, a method of deploying an anchor 100 will be described in more detail. As shown in FIG. 5A, an anchor portion 100 is secured within a distal end portion 120 of an anchor delivery catheter 122. The distal end portion 120 includes a distal end sheath 124 that surrounds the anchor portion 100 and maintains the anchor portion 100 in a compressed configuration during delivery to a treatment site. The anchor delivery catheter 122 may also includes an expandable structure such as an expandable balloon 126, which in the embodiment depicted is positioned around a portion of the distal end sheath 124.

Using the illustrated delivery system, the anchor delivery catheter distal end portion 120 containing the anchor portion 100 is advanced through a chest wall and through the cardiac tissue (or through other delivery routes) into a desired heart chamber. When the anchor portion 100 and surrounding distal end sheath 124 are advanced just in front of the orifice of the valve to be treated (such as a mitral valve or a tricuspid valve), the expandable balloon 126 can be expanded, as depicted in FIG. 5B. The expandable balloon 126 when expanded may be just a little smaller than the valve orifice, but larger than the distance between chordae tendinae and allow advancement of the anchor delivery catheter distal end portion 120 past the chordae tendinae and other sub-valvular structures by preventing the anchor delivery catheter distal end portion 120 from becoming entangled within or otherwise passing between such structures in an undesired manner.

Figures 5C, 5D:
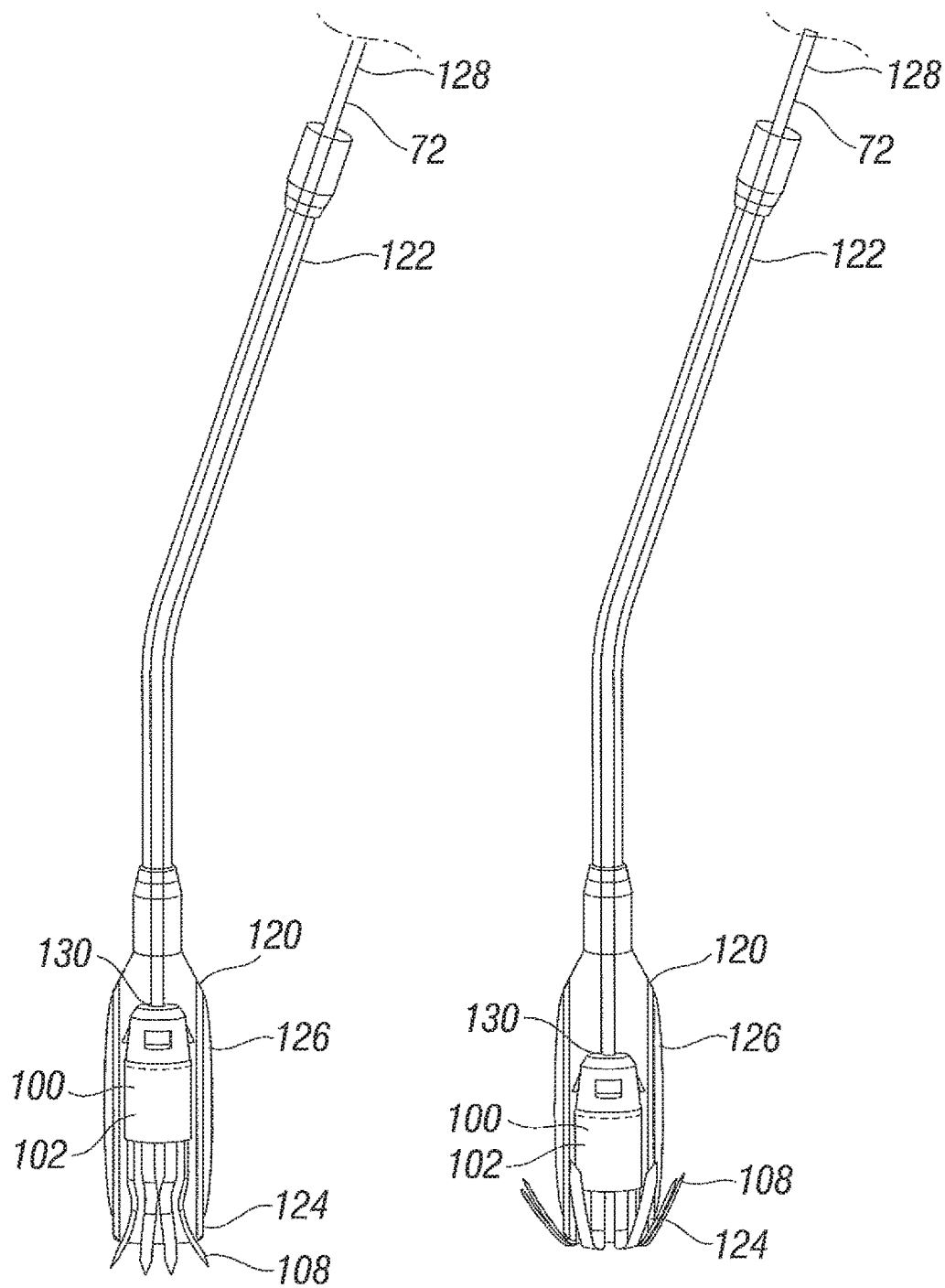

When the anchor delivery catheter distal end portion 120 is advanced such that the anchor portion 100 is properly positioned at a desired target location within the heart, the distal end sheath 124 opening remains in contact with the target location while the anchor portion 100 is pushed distally with respect to the distal end portion 120 by means of pushing on the rod 86 or 72 at the proximal end of the delivery catheter 122, as illustrated in FIGS. 5C and 5D. As the anchor portion 100 is exposed to the tissue, the prongs 108 expand outwardly. In some embodiments, the expansion of the prongs 108 to tissue may advantageously pull the anchor portion 100 out of the anchor delivery catheter 122 and outer sheath 126 and dig into the tissue by its inherent force. A light push forward on the delivery catheter 122 can enable a continuous tissue contact of the delivery catheter orifice 124 to ensure tissue contact with the prongs 108

After being released from the outer sheath 126, the prongs 108 on the anchor portion 100 may continue to expand, bending back around towards the generally tubular body 102 while grabbing nearby heart tissue. This tissue-engaging action by the prongs 108 can help to maintain the anchor portion 100 in a stable position within the heart that resists movement due to heart beats, blood flow, and similar actions. In this respect, the anchor portion 100 may at least partially "self-deploy" within the heart, requiring little or no extra pressure from the anchor delivery catheter 122 to anchor within the muscular wall of the heart. Note that although FIGS. 5C and 5D depict the expandable balloon 126 in a deflated condition during deployment (which may be preferable in some applications), the expandable balloon 126 (if present) may alternatively be left inflated during deployment of the anchor portion 100.

In the embodiments of FIGS. 5A-5D, the elongate member 72 took the form of an elongated rod-like structure 86 secured to the anchor portion 100 via an anchor portion connection in the form of a screw-like connection 130. The elongated rod-like structure 86 can be relatively thick and configured to transmit axially rotational movement along its length. When the user desires to remove the elongated rod-like structure 86, the user can rotate a proximal portion of the elongated rod-like structure 86 (or a proximal portion of a wire secured to the proximal end of the elongated rod-like structure 86, wherein the wire may be positioned outside of the patient's body), thereby causing a corresponding rotation of the distal portion of the elongated rod-like structure 86 and the screw-like connection 130 to the anchor portion 100. This rotation will essentially unscrew the screw-like connection 130, thereby disconnecting the elongated rod-like structure 86 from the anchor portion 100.

The elongate member 72, such as the elongated rod-like structure 86 depicted, can also serve to retract the anchor portion 100 back into the distal end sheath 124 during or after deployment thereof. For example, in the event that the user is not satisfied with the initial deployment of the anchor portion 100, the user can pull on the elongated rod-like structure 86 while holding still or even advancing the distal end sheath 124. As the anchor portion 100 is drawn back into the distal end sheath 124, inward pressure on the prongs 108 from the distal end sheath 124 will cause the prongs 108 of the anchor portion 100 to collapse inwardly, thereby collapsing the anchor portion 100 back to its delivery (i.e., predeployment) condition as the anchor portion 100 is pulled back into the distal end sheath 124. The user can then redeploy the anchor portion 100 in a new position, or can remove the anchor portion 100 entirely from the patient.

Note that the anchor portion can be implanted without having the elongate member attached thereto during the implantation procedure. In such embodiments, the elongate member could be secured to the anchor portion after the anchor portion is deployed. In another embodiment, the anchor portion can be deployed with an elongate member secured thereto, but then after the implantation a surgeon or other user could remove the original elongate member and replace it with a substitute elongate member. Also, if a relatively stiff elongated member 86 with a screw attachment 130 to the anchoring portion 100 is used, a thread elongated member 72 may be attached to the anchoring portion permanently while the stiff elongated member 86 is detached.

Figure 6:
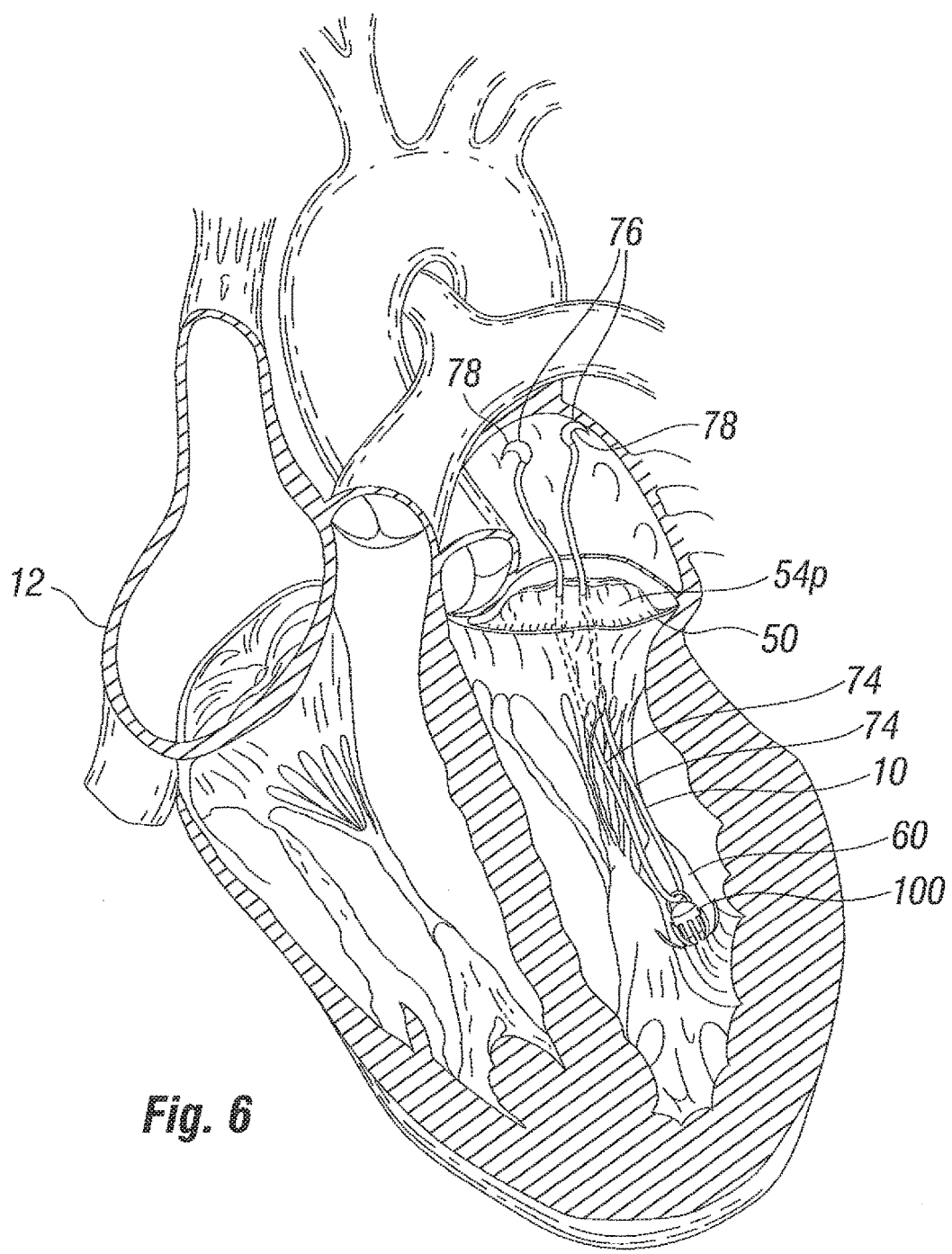
FIG. 6 illustrates an embodiment of the invention during implantation wherein a suture thread is stitched through the anterior mitral valve leaflet to create replacement chordae tendinae.

FIG. 6 depicts an embodiment of a chordae tendinae replacement procedure using a device 10 according to an embodiment of the invention, wherein an anchor 100 is shown after deployment in a papillary muscle 60, thereby completing the first stage of the implantation procedure. The two free ends 76 of the suture threads 74 can then be passed (via, e.g., needles 78) through a leaflet (which is a posterior leaflet 54p in the particular embodiment depicted) of the mitral valve 50 (or other tissue, depending on the particular application) by the surgeon or other user. After determination of the length of the hereby created chordae tendinae, the threads 74 are knotted or locked by other fixation means like a suture clip or locking mechanism. Note that the device could be used to replace chordae tendinae of the posterior leaflet 54p and/or anterior leaflet 54a of the mitral valve 50, or of any other leaflet of other valves.

Figure 7:
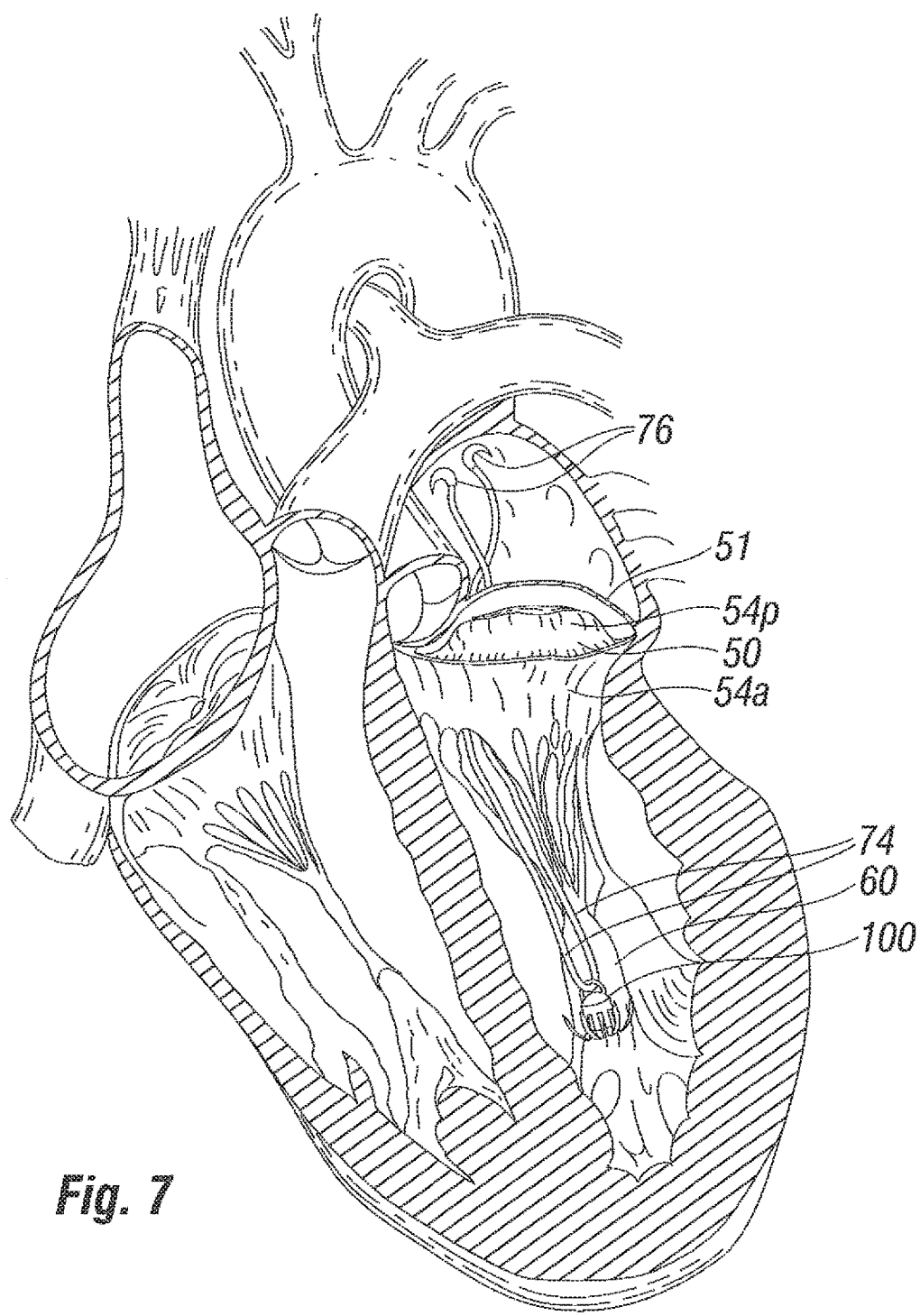
FIG. 7 illustrates a device wherein suture is stitched through the mitral valve annulus for pulling the papillary muscle closer to the annulus, thereby relieving strain on the chordae tendinae according to an embodiment of the invention.

With reference to FIG. 7, in ischemic heart disease caused by clogged arteries to the heart muscle, a papillary muscle 60 may have moved away from the mitral valve annulus 51 and thereby be pulling the corresponding leaflet down into the ventricle. The two leaflets 54a, 54p can no longer meet properly, and regurgitation through the valve 50 may occur. In such a case, the anchor can be deployed at or adjacent to the papillary muscle, and one or more of the suture ends 76 may be attached to the valve annulus 51 (instead of to the valve leaflets 54a, 54p), thereby shortening the distance between the displaced papillary muscle 60 and the annulus 51 and thereby allowing the leaflets 54a, 54p to meet again and the valve 50 to again be competent.

Figure 8A:
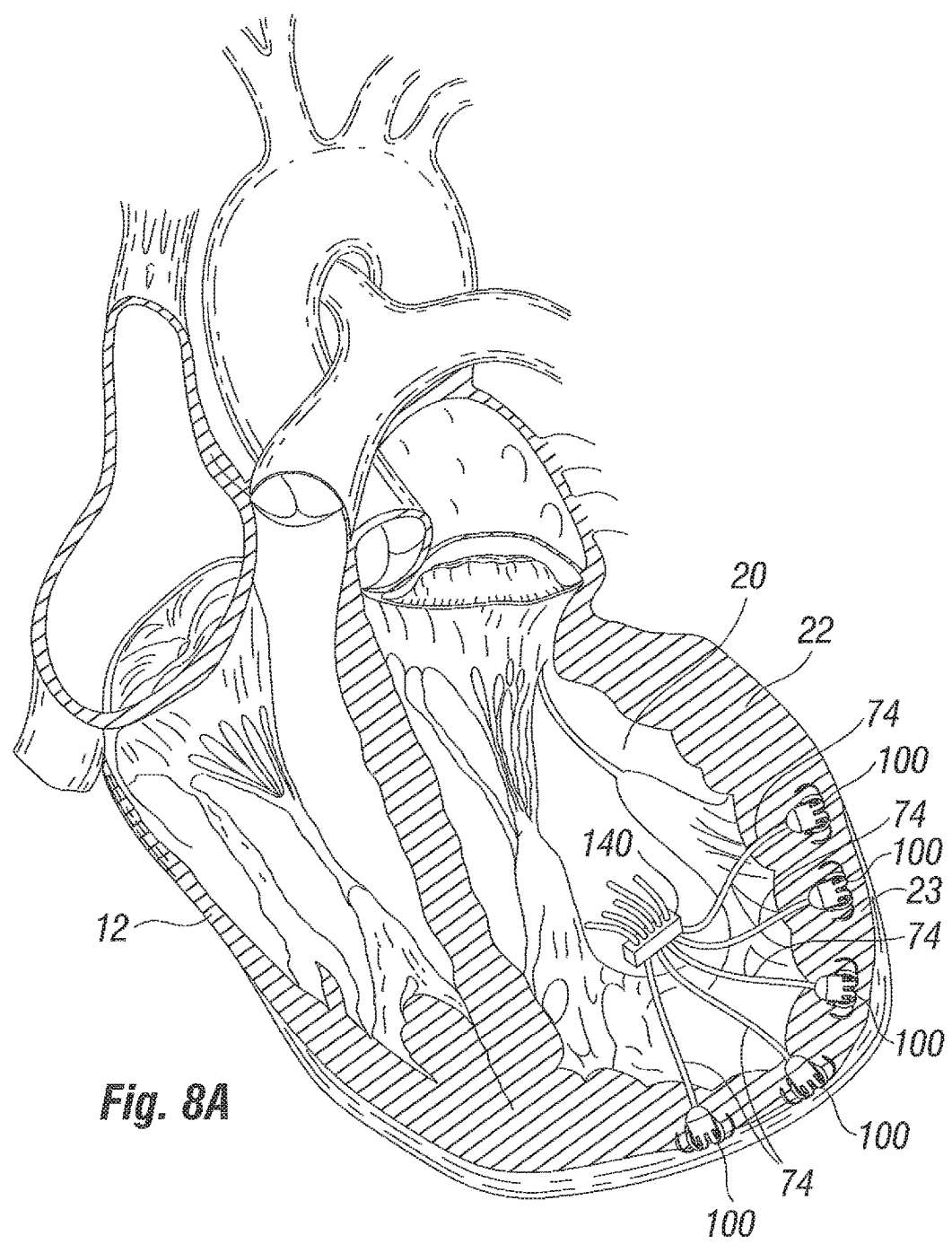
FIG. 8A illustrates anchors are configured for engaging the inner wall of the left ventricle and aneurysms according to an embodiment of the invention.
Figure 8B:
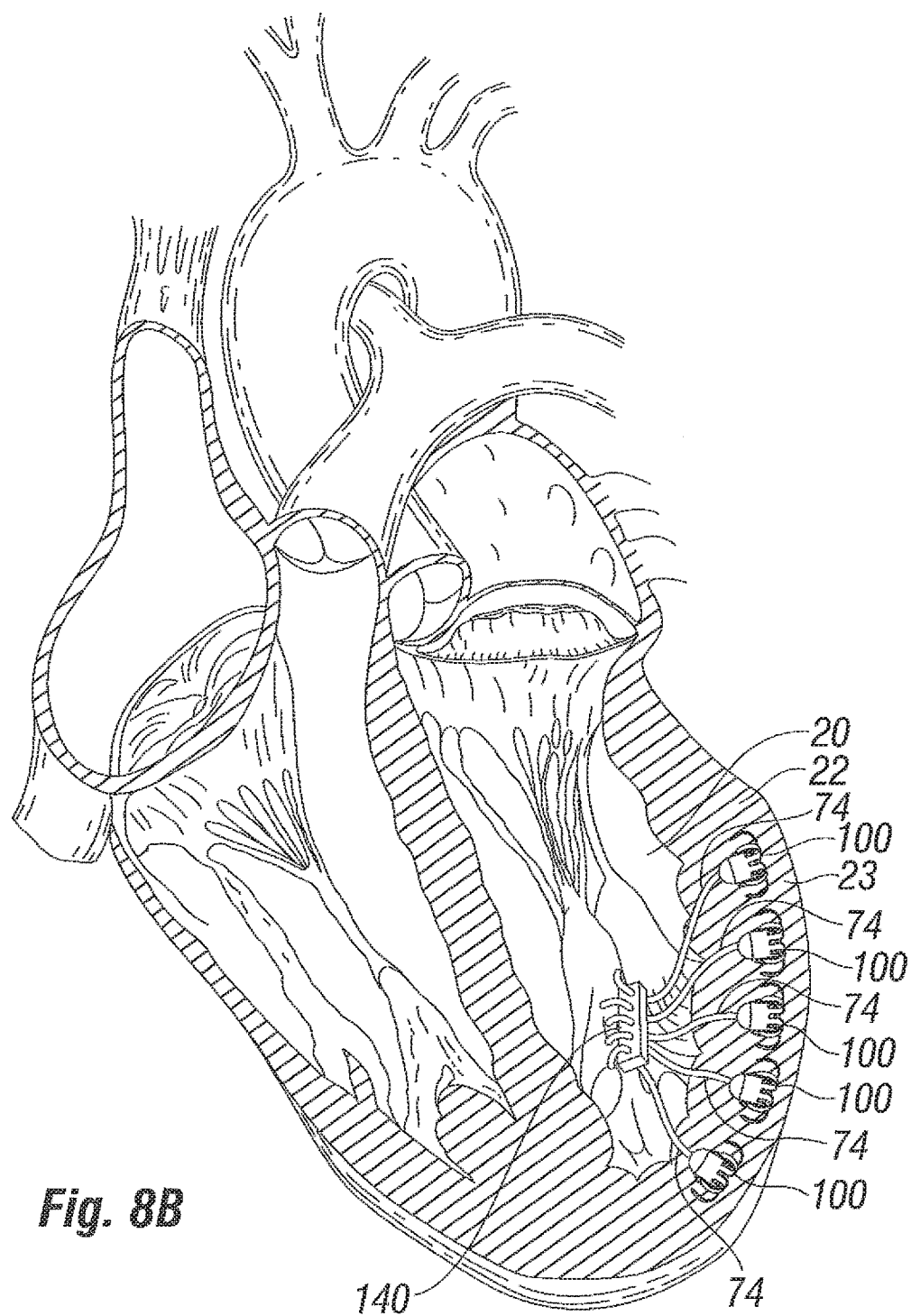
FIG. 8B illustrates the device of FIG. 8A after foreshortening and locking the threads for reshaping the left ventricle according to an embodiment of the invention.

FIGS. 8A and 8B depict a method of treating myocardial infarction, a condition which occurs regularly after blockage of the arteries, resulting in heart muscle cell death. As a result thereof, in many cases a weakening of a portion of the heart wall 22 or other structure may occur, with a corresponding bulge or other structural deformation to the heart portion. For example, in a heart 12 having a weakening of the heart wall 22 in the areas adjacent the left ventricle 20, a considerable dilation or bulge can occur in the left ventricular wall area 23. With each heart contraction in systole, the left ventricle 20 will bulge outwards instead of properly contracting, causing less blood to leave into the aorta and thereby causing low cardiac output and heart failure. The current invention may be used to treat this condition. As illustrated in FIG. 8A, in one method of use multiple anchors 100 may be deployed in the left ventricular wall area 23. The suture threads 74 can be collected in the center by means of a knot or other locking mechanism (such as a suture clip 140) and each thread 74 may be pulled inwards toward the center until the bulging is adequately reduced. The suture threads 74 or other elongate members are then locked via the knot or other locking mechanism to maintain the left ventricle 20 in the reshaped condition, as depicted in FIG. 8B.

Figure 8C:
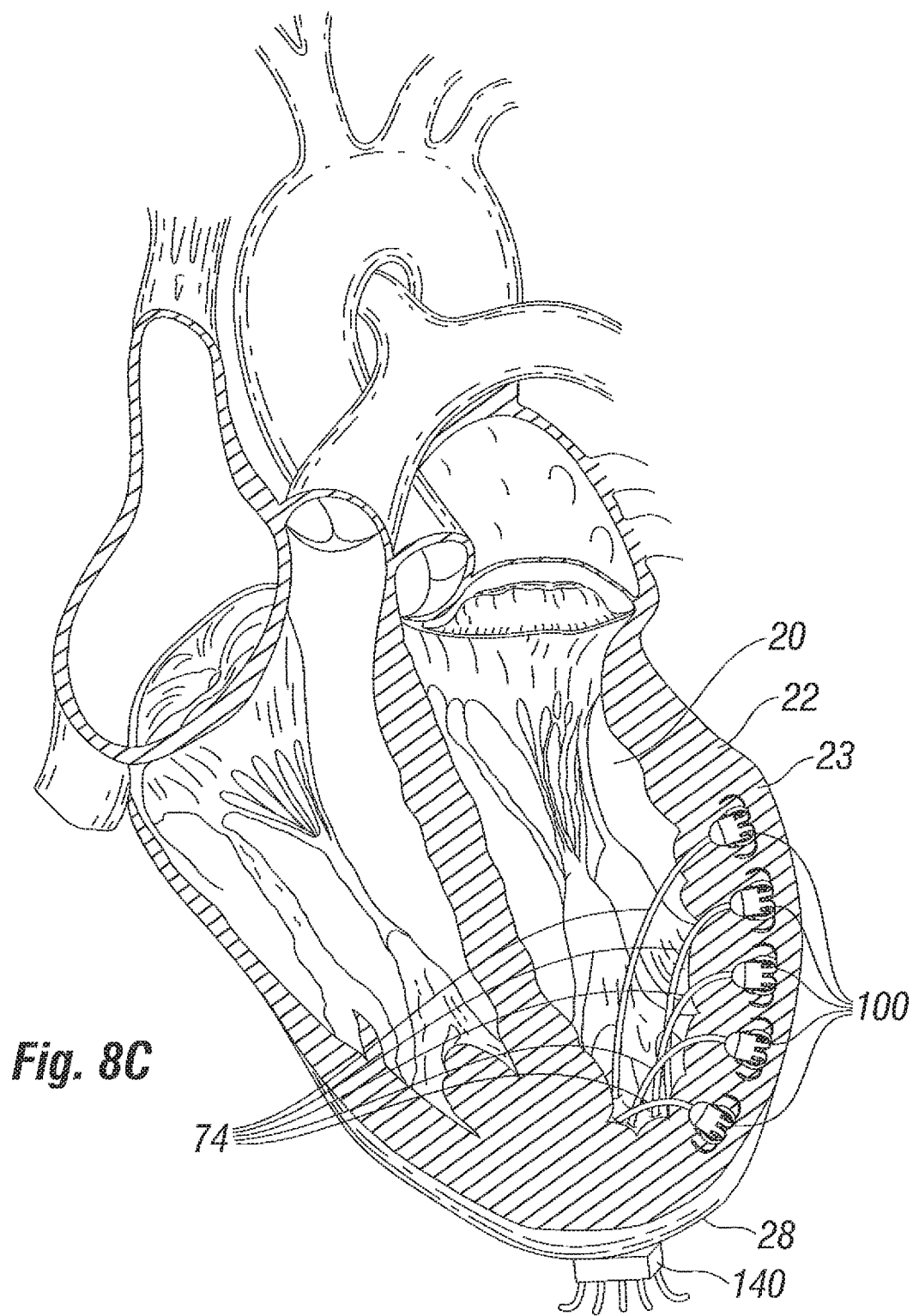
FIG. 8C illustrates an embodiment of the invention wherein the threads are captured and held in a locking mechanism located outside the left ventricle.

FIG. 8C illustrates an alternative configuration for treating a weakened heart wall area 23, wherein the threads 74 are pulled and locked at a location outside of the heart wall 22. In the particular embodiment depicted, the suture clip 140 is positioned at the apex 28.

Figure 8D:
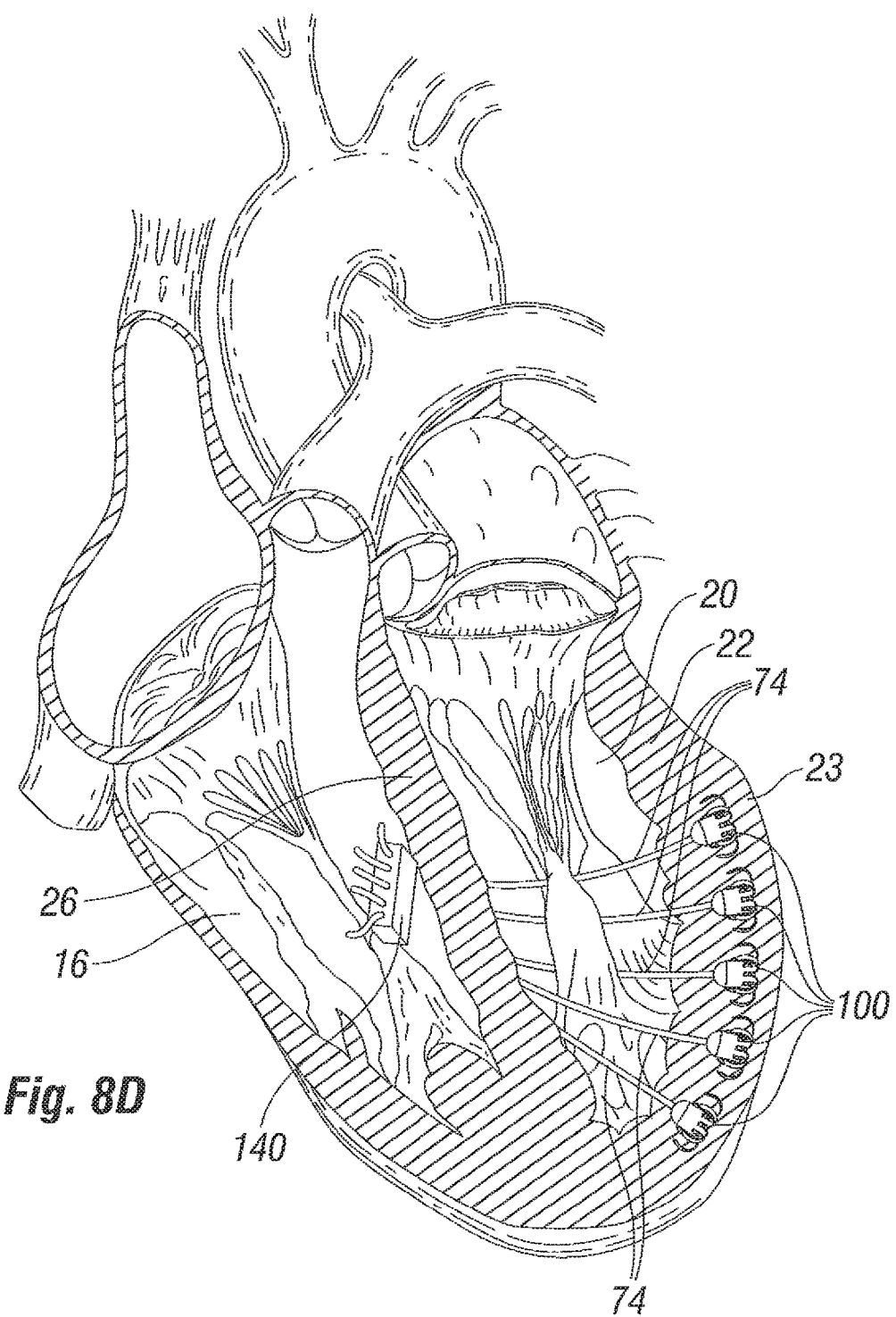
FIG. 8D illustrates an embodiment of the invention wherein the threads are captured and held in a locking mechanism located in the right ventricle along the interventricular septum.

FIG. 8D illustrates a further embodiment of the invention, wherein the suture threads 74 are passed through the ventricular septum 26 and into the right ventricle 16. The suture threads 74 are then collected on the opposite (i.e., right ventricle) side of the ventricular septum 16, and each thread 74 may be pulled until the bulging is overcome. The suture threads 74 can then be locked in the desired position by means of a locking mechanism, such as the suture clip 140 depicted. A similar treatment may also be applied to papillary muscles that have dislocated outwards due to myocardial infarction, thereby causing the mitral valve to leak. A thread or threads may be passed through the papillary muscle and then through the ventricular septum. As the thread or threads are tightened, they will cause inwards movement of the papillary muscle and thereby cause the mitral valve to be competent again, at which point the thread or threads can be locked on the right side of the septum by means of a locking mechanism, e.g., a knot or other fixation mechanism.

Figure 9:
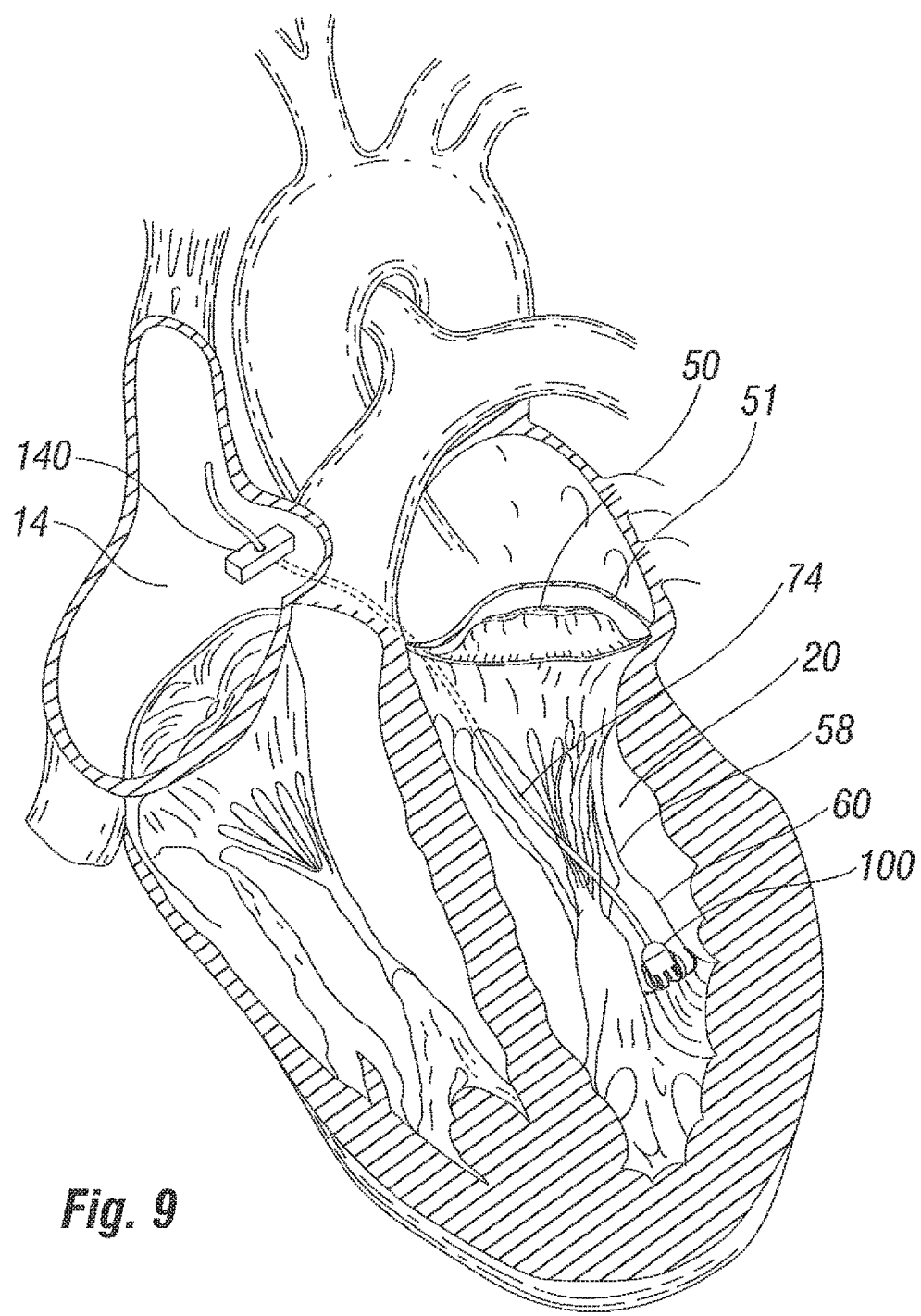
FIG. 9 illustrates a further embodiment of the invention wherein the anchor of the suture is deployed inside a papillary muscle and the elongate member (e.g., thread) is locked inside the right atrium close to the annulus of the mitral valve, thereby closing the papillary muscle to the annulus and relieving tension on the chordae tendinae.

With reference now to FIG. 9, another alternative embodiment is illustrated wherein the anchor 100 is deployed inside a papillary muscle 60, and the elongate member 72 (e.g., suture thread 74) is locked via a suture clip 140 inside the right atrium 14, e.g., at a location close to the annulus 51 of the mitral valve 50, thereby pulling the papillary muscle 60 toward the annulus 51 and relieving pressure on the chordae tendinae 58. Such a suture arrangement could treat left ventricular bulging, papillary muscle displacement and mitral regurgitation simultaneously.

Figure 10A:
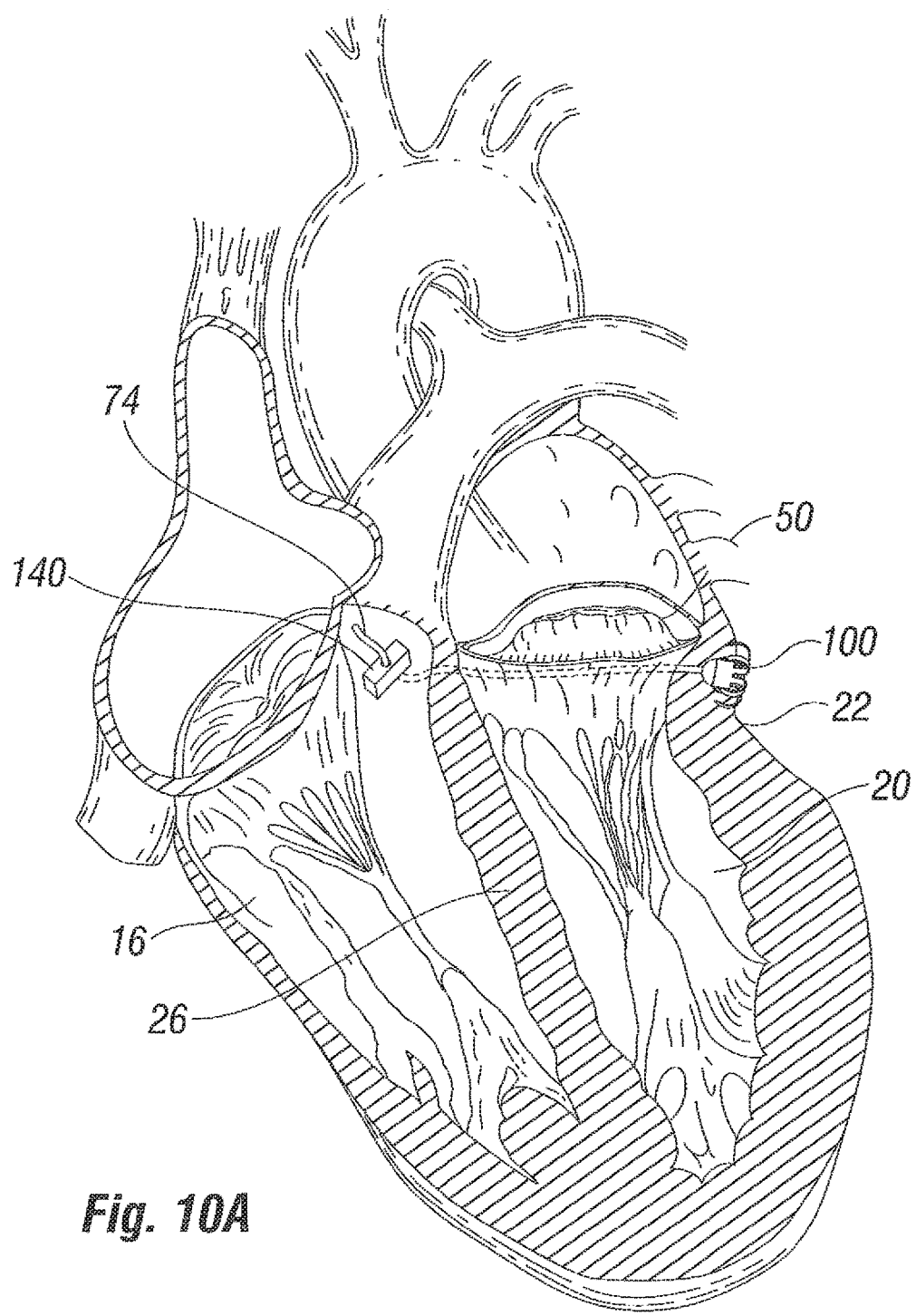
FIG. 10A illustrates a further embodiment of the invention wherein the anchor is located just below the mitral valve in the left ventricle wall and the locking mechanism is located in the right ventricle on the septum, thereby pulling the posterior leaflet from lateral towards the septum and shortening the antero-posterior diameter (also called septolateral distance) for repairing a mitral valve leak.

With reference to FIG. 10A, another alternative embodiment is illustrated wherein an anchor 100 is deployed in the heart wall 22 just below the mitral valve 50, and the suture thread 74 (or other elongate member) is locked via a suture clip 140 in the right ventricle 16 on the interventricular septum 26, with tension in the suture thread 74 pulling the posterior mitral leaflet 54p from lateral towards the interventricular septum 26 and thereby shortening the antero-posterior diameter of the mitral valve annulus 51 to repair a mitral valve leak. Similarly (not shown) an anchor may be deployed in the heart wall adjacent the left atrium, just above or otherwise adjacent the mitral valve, adjacent to or in the mitral valve annulus, and the suture thread (or other elongate member) can be locked via a suture clip in the right atrium on the atrial septum, with tension in the suture thread pulling the posterior mitral leaflet from lateral towards the atrial septum and thereby shortening the antero-posterior diameter of the mitral valve annulus to repair a mitral valve leak.

Figure 10B:
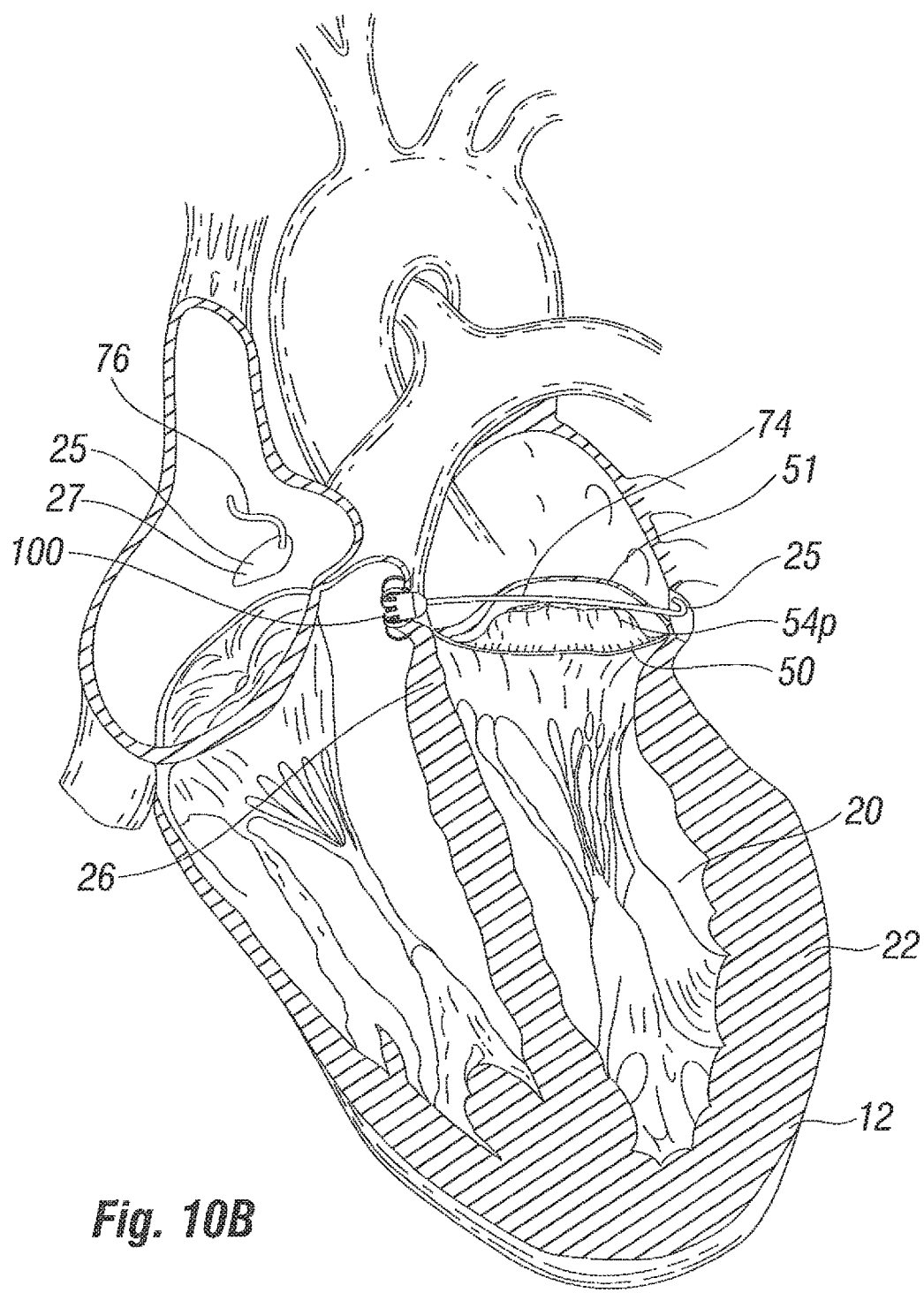
FIG. 10B depicts an embodiment of the invention wherein the anchor is located close to the mitral valve in the ventricular septum and the thread is running through the coronary sinus and the elongate member (e.g., thread) is locked inside the coronary sinus, in the orifice of or just outside the coronary sinus orifice, thereby pulling the posterior leaflet from lateral towards the septum and shortening the anterior-posterior diameter for repairing a mitral valve leak.

With reference to FIG. 10B, yet another embodiment is illustrated wherein the anchor 100 is located adjacent the mitral valve 50. The particular embodiment of FIG. 10B depicts anchor deployment in the interventricular septum 26, although other deployment locations (such as in the heart wall 22 in an area adjacent an upper portion of the left ventricle 20) are also within the scope of the invention. The anchor 100 may be deployed by means of a catheter (such as the delivery catheter 122 from FIGS. 5A-5D) from inside the coronary sinus 25. With the catheter distal end 120 positioned in a distal portion of the coronary sinus (or other desired deployment location) and the opening of the distal end sheath 124 held against the inner wall of the coronary sinus, the anchor 100 can be advanced out of the distal end sheath 124 so the prongs 108 are exposed to the coronary sinus wall and released to dig into the left ventricular wall 22 through the coronary sinus wall. The elongate member 72 in the form of a suture thread 74 passes from the anchor 100 and runs along the inside of the coronary sinus and extends out from the ostium 27 of the coronary sinus 25 into the right atrium, thereby at least partially encircling the mitral valve annulus 51. The free end 76 of the suture thread 74 is locked in or outside of the coronary sinus 25 by means of a suture knot or lock (not shown), pulling the mitral valve posterior leaflet 54p from lateral towards the interatrial septum 24 and thereby shortening the antero-posterior diameter of the mitral valve annulus 51 to repair a mitral valve leak.

Those skilled in the art will appreciate that the treatments described herein may demand robust attachment strength. For example, when treating dilation of the left ventricle, the forces on the threads and the anchors are large due to the high blood pressure in the left ventricle and the high wall stress due to the large diameter of the bulging sack. In such cases, a two stage procedure might be preferred. For two-stage procedures (i.e., procedures where the anchor is deployed separately from the elongate member), the device may be provided with a coupling member to attach and/or release the elongate member to/from the anchor. The coupling member provides a point of attachment for connecting an elongate member, such as a suture thread, to the anchor during a second or later implantation stage. During the second stage, the thread portion may be delivered into the heart by means of a catheter-based technique, similar to that described above with respect to FIGS. 5A-5D. However, in the second stage of a multi-stage delivery, the elongate member is delivered into the heart using a delivery catheter and is subsequently coupled to the previously-deployed anchor or to a first part of another elongate member already attached to a coupling member of the pre-deployed anchor.

Figure 11:
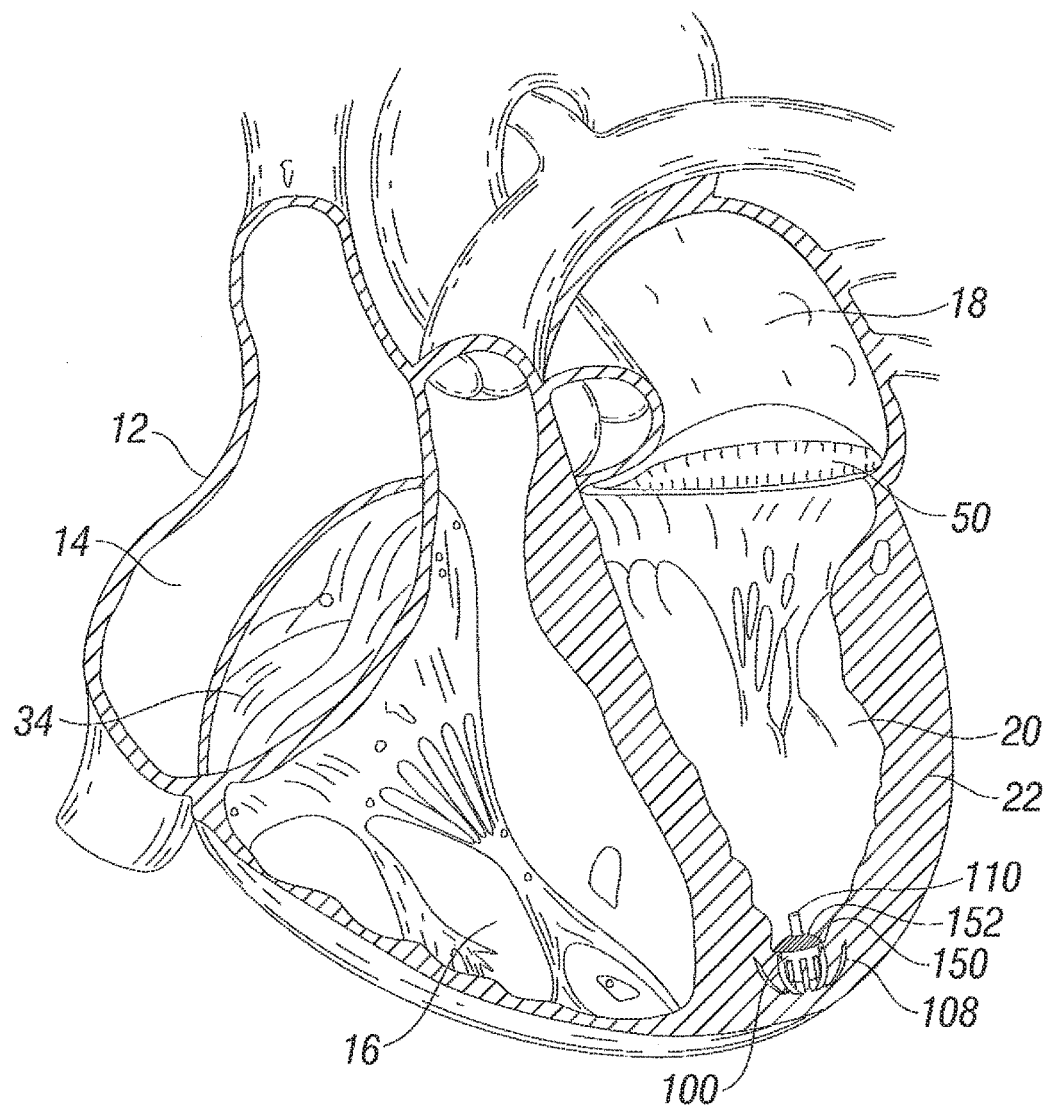
FIG. 11 depicts an anchor deployed in a heart according to an embodiment of the invention.

With reference now to FIG. 11, an anchor portion 100 is shown some time after anchor deployment into the muscular heart wall 22 of the left ventricle 20 (i.e., after the first stage of the implantation procedure). After implantation in the heart 12, endocardial tissue 150 has grown over the exposed tubular portion 152 of the anchor portion 100 that is protruding from the muscular wall 22 into the left ventricle 20, preferably leaving only the anchor coupling member 110 exposed within the left ventricle 20. Simultaneously, inside the heart wall 22 around the embedded portions of the anchor portion 100 a scarring healing takes place, wherein fibrocytes create strong scarring tissue surrounding the prongs 108, thereby integrating them with the muscle of the heart wall 22 to create a very strong attachment. It has been found that adequate tissue overgrowth on the exposed areas of the anchor portion 100 and the scar healing around the prongs 108 may occur in two or three weeks. However, the amount of time required may depend on various factors, such as the location of the anchor portion 100 within the heart 12, the surface features or coatings of the anchor portion 100, and finally the health status and other characteristics of the patient.

The coupling member 110 provides a point of attachment for connecting an elongate member 72 (such as the suture threads 74 and rod-like members 86 previously described embodiments) during a second or later implantation stage. Note that FIG. 11 does not depict an elongate member (such as a suture thread 74 or rod-like member 86 from earlier embodiments) as being present—the reason being that the elongate member is to be attached as a second or later stage of a multi-stage procedure. While a user may be able to couple the elongate member to the previously-deployed anchor portion by simply searching around the patient's heart, additional techniques can be used to facilitate this procedure. For example, both the coupling member on the anchor and an attachment mechanism of the thread portion may be magnetized, thereby allowing the two to be drawn together when in close proximity. In still another example, a vacuum-assisted connection can be used to facilitate connection of the elongate member to the anchor. As another example, anchor lines could be used, such as where an anchor line (e.g., a suture thread) is left secured to the coupling member of the anchor during the first implantation stage (i.e., anchor deployment) and left within the patient for use during the second stage (i.e., attaching the elongate member to the anchor). During the second implantation stage, the locking mechanism of the elongate member portion can be advanced along the guide element (e.g., originally-deployed suture thread or wire, etc.) until the locking mechanism reaches the coupling member of the previously-deployed anchor.

During the second or later stage, the elongate member 72 may be delivered into the heart using a multi-stage procedure similar to that depicted in FIGS. 12A-12D, wherein an anchor portion 100 is deployed in the first stage, and then the elongate member 72 is advanced to the site and connected to the anchor portion 70 in situ.

Figure 12A:
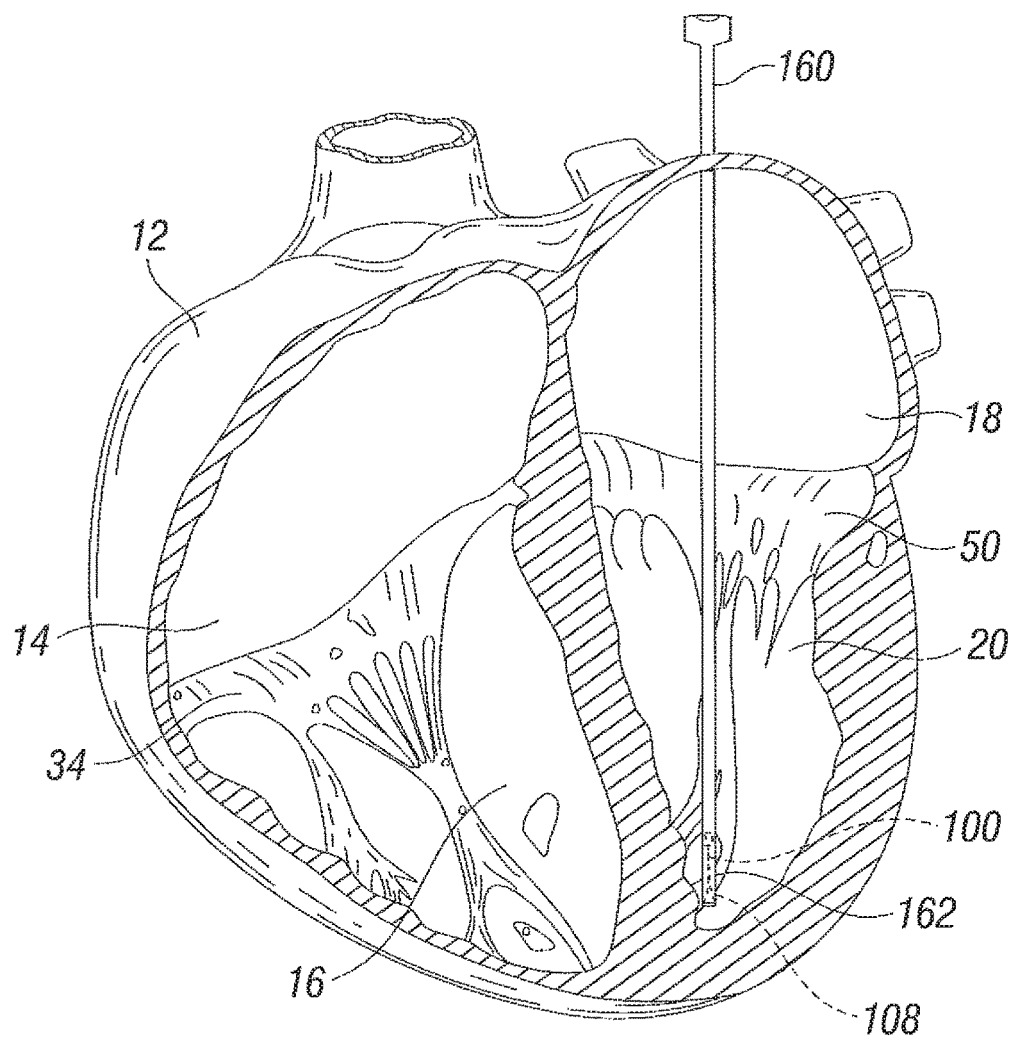
FIGS. 12A-12D depict a method for deploying a device according to an embodiment of the invention.

In FIG. 12A, an anchor deployment catheter 160 is shown having a distal end 162 advanced to a desired deployment site within the left ventricle 20. The anchor portion 100 is positioned at the anchor deployment catheter distal end 162, and more specifically is contained within the anchor deployment catheter distal end 162. The anchor portion 100 includes multiple anchor members 108 configured to expand outward and embed within the heart tissue when released from the anchor deployment catheter 160, which can be accomplished by pushing the anchor portion 100 out of the anchor deployment catheter 160 and/or withdrawing the anchor deployment catheter 160 from around the anchor portion 100.

Figure 12B:
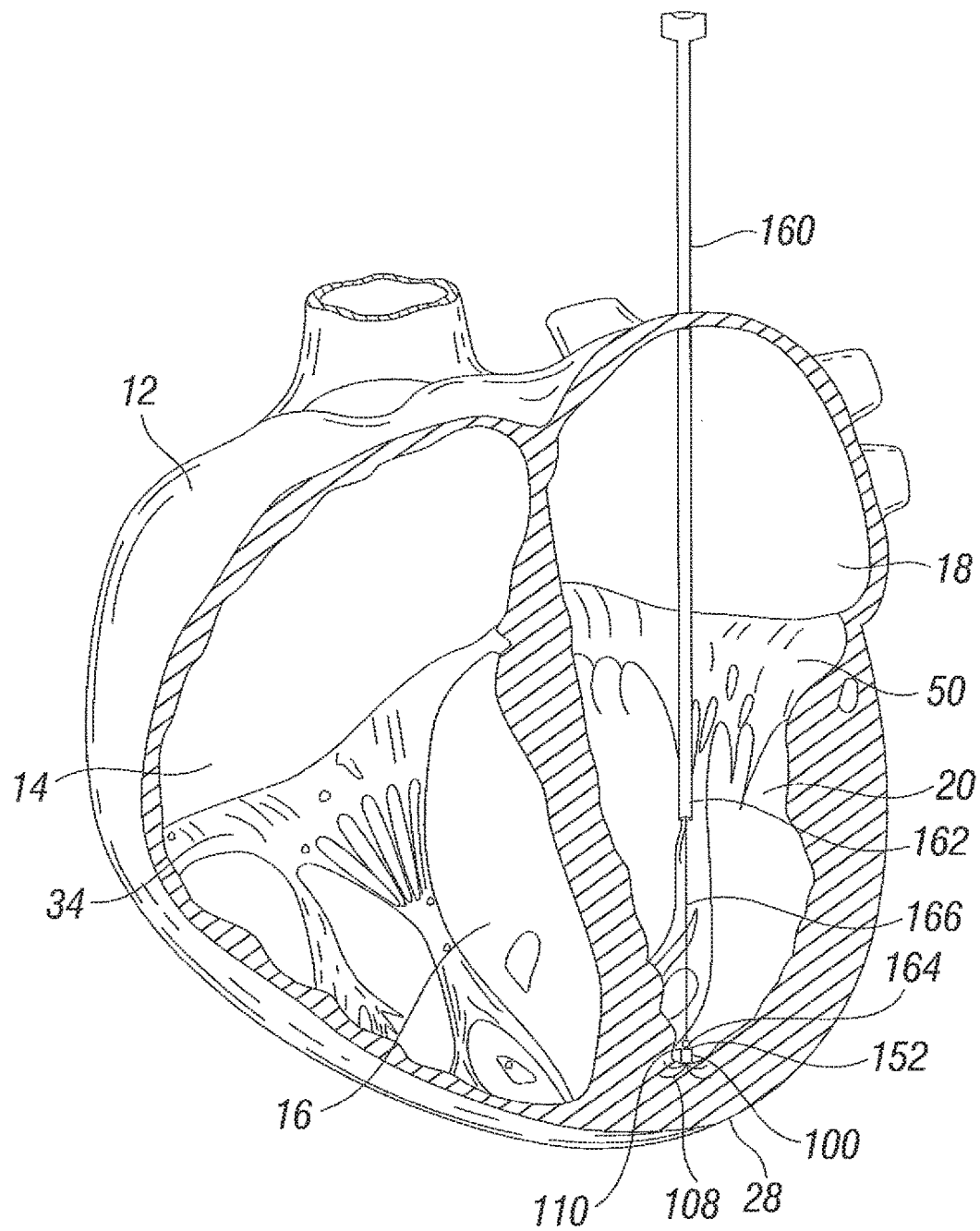

In FIG. 12B, the anchor portion 100 has been deployed, with the anchor members 108 embedded into the heart tissue in the lower portion of the left ventricle 20 adjacent the apex 28. The anchor portion 100 has a top portion 152 having an anchor connector 110 configured to received a mating connector from an elongate member which will be deployed in the second stage (discussed below). The anchor portion 100 also includes an anchor line opening 164, which is a loop or lumen through which an anchor line 166 can be passed. The particular anchor line 166 depicted in FIG. 12B is a line of suture that passes into the patient and into the heart 12, passes through the anchor line opening 164, and then passes back out of the heart 12 and the patient to form a double suture line. As the anchor deployment catheter 160 is removed from the heart 12, the anchor line 166 is left trailing from the anchor portion 100 and out of the heart 12 and patient. While allowing the anchor portion 100 to heal in over some time, the free ends of the anchor line might also be left under the skin of the patient and then retrieved when needed.

Figure 12C:
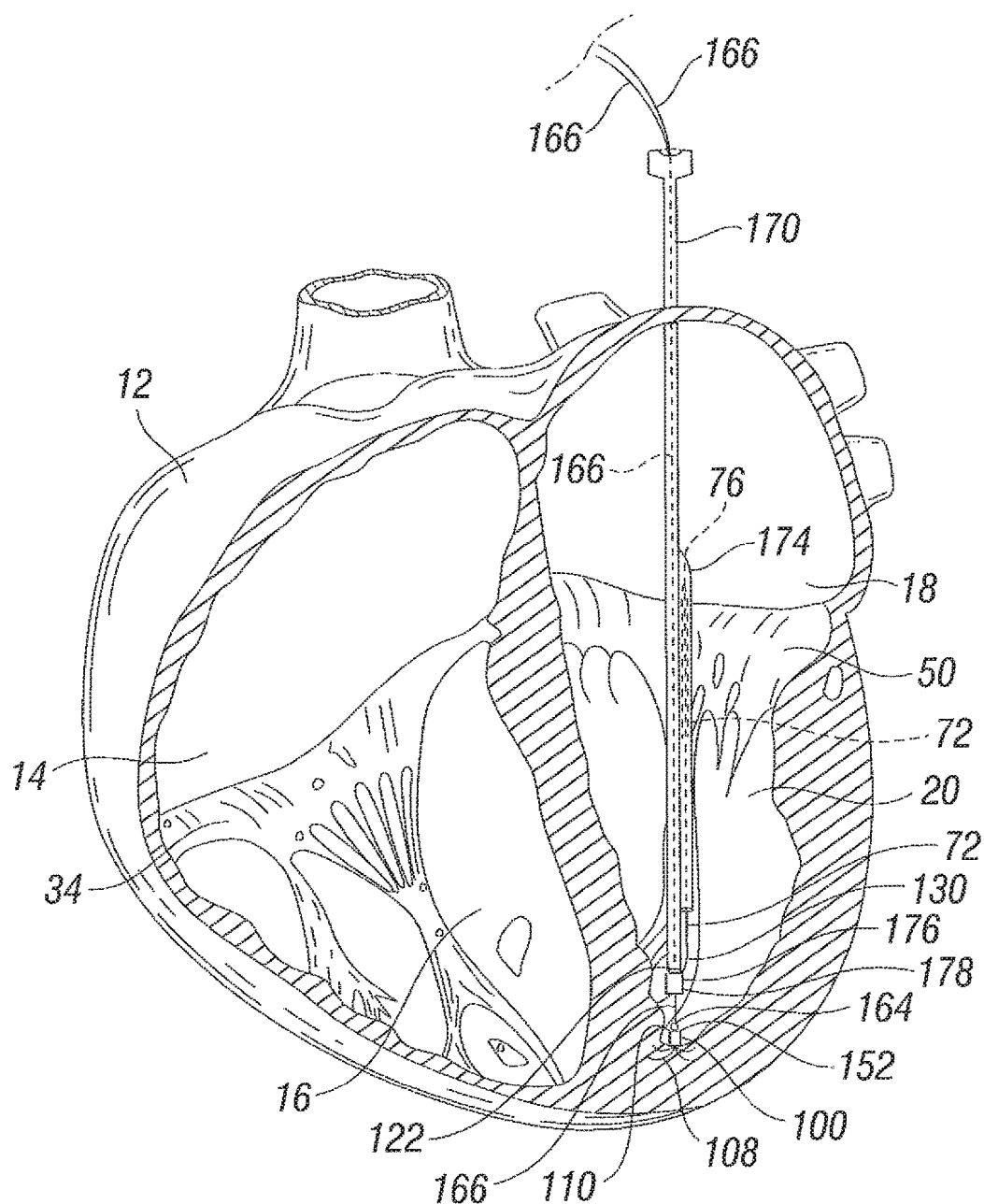

FIG. 12C depicts the second stage of the deployment procedure, wherein the elongate member 72 is advanced into the heart 12 and secured to the anchor portion 100. A second deployment catheter 170, to which is secured an elongate member 72, is advanced to the area in the left ventricle 20 at or adjacent the previously-deployed anchor portion 100. In the particular embodiment depicted, the second deployment catheter 170 is an over-the-wire type catheter having an inner lumen configured to permit the anchor line 166 to slidingly pass therethrough. Note, however, that a so-called rapid-exchange type of delivery catheter could also be used. The second deployment catheter 170 includes a canopy container in the form of a side pocket 174 configured to contain and restrain the elongate member 72 during delivery.

As depicted in FIG. 12C, the second deployment catheter 170 is advanced along the anchor line 166 to the anchor portion 100. The elongate member 72 includes a distal end 176 having a connector 178 configured to be secured to an anchor portion connector 110 on the exposed upper surface 152 of the anchor portion 100. As the second deployment catheter 170 is advanced along the anchor line 166, the elongate body portion distal end 176 and connector 178 will be led into alignment and contact with the anchor portion connector 110. When the elongate body portion connector 178 contacts the anchor portion connector 110, the two connectors 110, 178 are connected together. Note that many different types of connectors are within the scope of the invention, and the particular connectors used with a particular device may be a matter of choice. The connectors may be snap-type or quick-connect connections which automatically connect when the two connectors are brought into contact. The connectors may be manually operated, and/or may include a release device to permit disconnection at a later time.

Figure 12D:
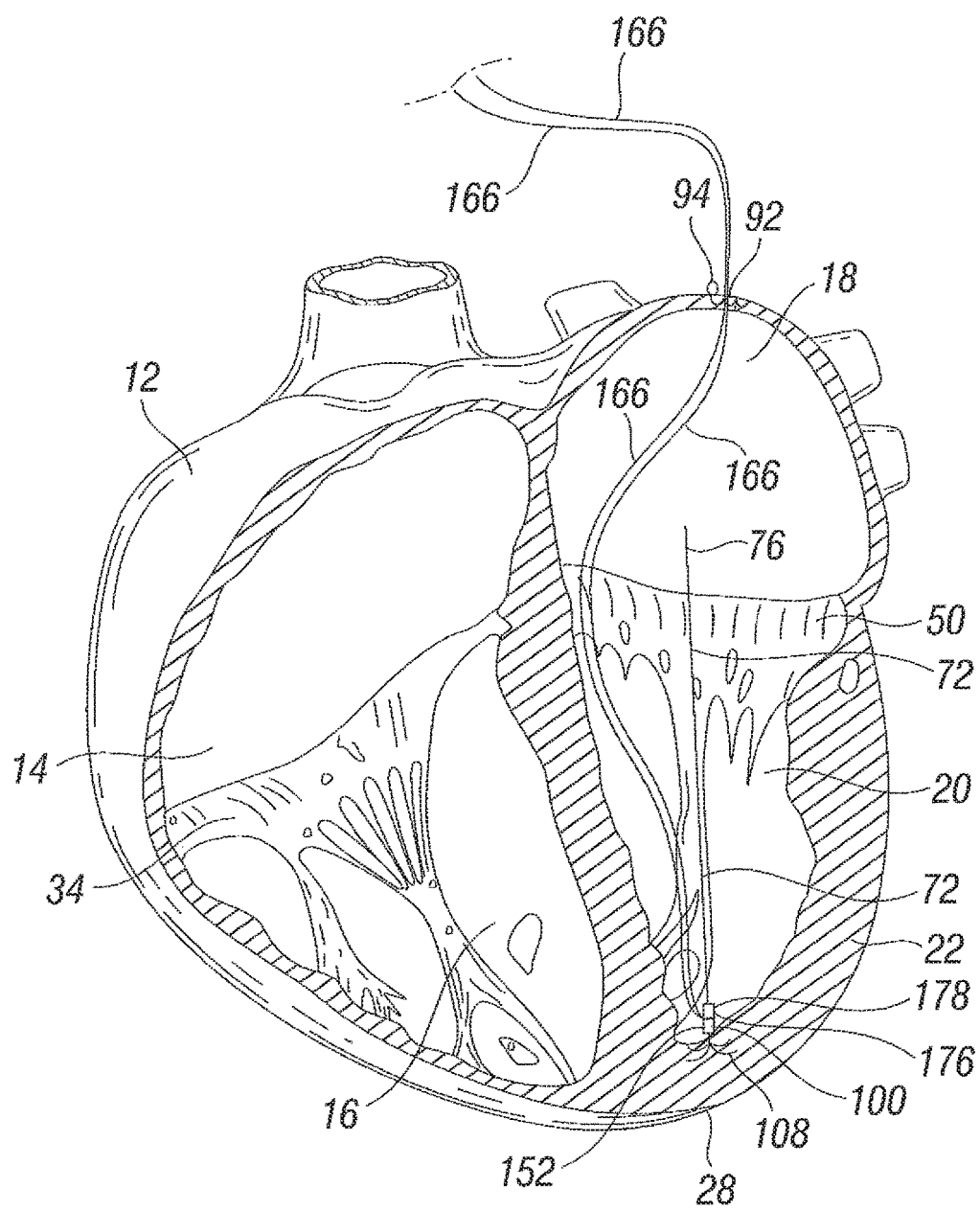

Connection of the two connectors 110, 178 effectively secures the anchor portion 100 to the elongate member 72. Once the two connectors 110, 178 are connected, the second deployment catheter 170 can be withdrawn, which will release the elongate member 72 from the side pocket 174 to deploy the elongate member 72, as depicted in FIG. 12D. In the particular method depicted, the anchor line 166 is still depicted in position passing through the anchor line loop 164 (although the anchor line 166 could have been removed along with, or even prior to, removal of the second deployment catheter 170). The anchor line 166 can now be removed, which in the case of the double suture line depicted can involve releasing one end of the line that passes outside of the heart, and pulling on the other end passing outside the heart. The loose end of the double suture line will thus be pulled into the heart 12 and will be pulled out of the anchor line loop 164, thus releasing the anchor line 166 from the anchor portion 100. The free end 76 of the elongate member 72 can be secured to the desired tissue (e.g., a valve leaflet) to complete deployment of the device 10. The opening 92 through which the catheters 160, 170 were advanced into and removed from the heart 12 can be closed using a purse-string suture 94.

Note that a two-stage deployment device and method such as that depicted in FIGS. 12A-12D could be useful for situations where a user may desire to replace an initially-deployed elongate member. For example, if after the device is entirely deployed in a patient's heart, a user may determine that the initially-deployed elongate member is not of the optimal size/configuration or not optimally secured to desired tissue. Such situations may arise where one or more portions of the patient's heart (e.g., the valve, etc.) has deformed since the initial deployment procedure. In such a situation, a user could remove the initially-deployed elongate member while leaving the anchor portion in place. The user could then attach another elongate member to the anchor portion, and secure the free ends of the elongate member as desired. Alternatively, the user could simply leave the initial anchor portion in place without attaching another elongate member thereto. The user could also deploy a second elongate member using a second anchor portion.

Deployment of the device and/or of specific elements thereof, including navigation of the elongate member to connect to a previously-deployed anchor, can be facilitated with cameras, X-rays, or similar techniques which allow the user to visualize the device elements within the patient.

Figure 13A:
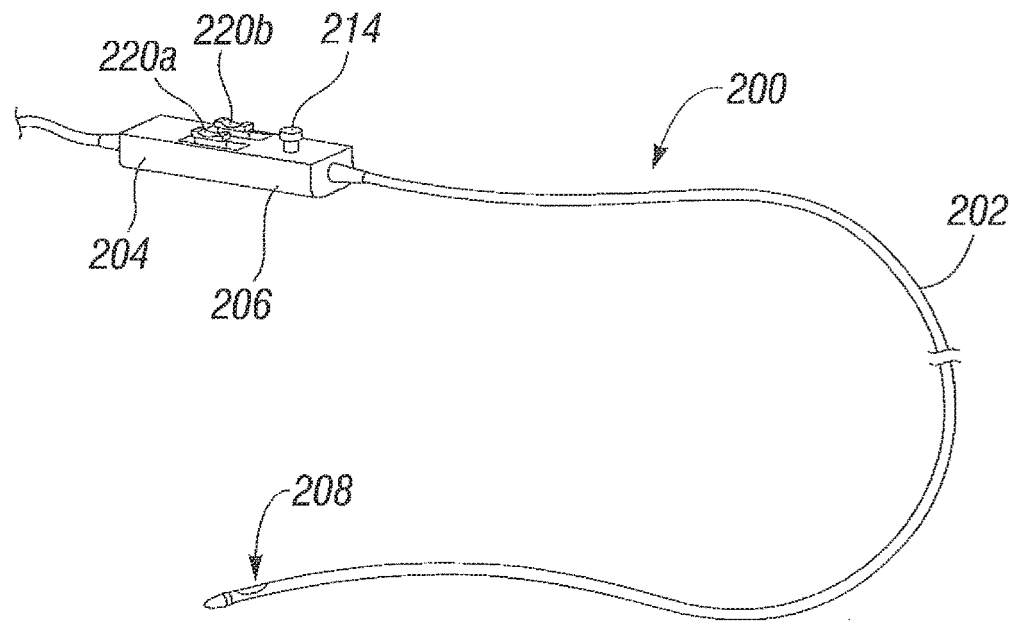
FIG. 13A is a perspective view of a suture deployment device according to an embodiment of the invention.

FIG. 13A depicts a suture deployment device 200 for use in deploying an elongated member, such as a suture line, into a valve leaflet. The suture deployment device 200 comprises an elongated body 202, a proximal end 204 having a handle 206, and a distal end 208.

Figure 13B:
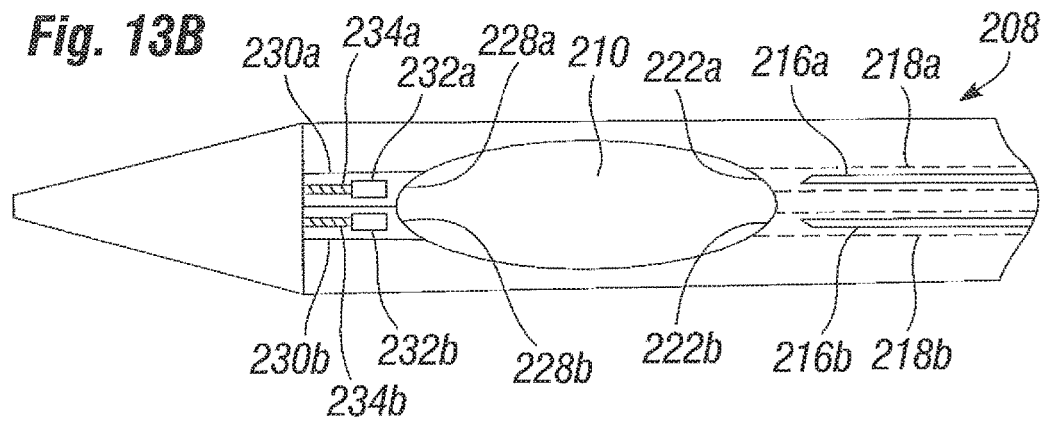
FIGS. 13B and 13C are top and side views, respectively, in partial cross section of the distal portion of the suture deployment device of FIG. 13A.
Figure 13C:
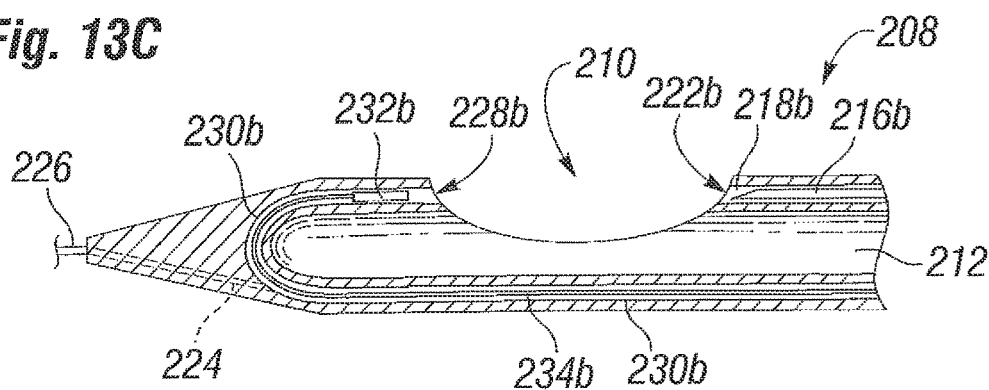

FIGS. 13B-13C depict a close-up views of the distal end 208 of the suture deployment device 200. A vacuum port 210 is positioned on a side of the distal end 208 and is in fluid communication with a suction lumen 212 passing the length of the suture deployment device and configured to be attached at the device proximal end 204 to a vacuum source (not shown). The vacuum applied to the vacuum port 210 is controlled by a user via one or more controls 214 positioned on the handle 206. Two needles 216a, 216b are positioned in needle lumens 218a, 218b and configured to be advanced and retracted across the vacuum port 210. The needles 216a, 216b may be independently controlled for separate advancement and retraction. In the particular embodiment depicted, the needles 216a, 216b are coupled to or otherwise in communication with actuators 220a, 220b located on the device handle 206. The forward and rearward movement of the actuators 220a, 220b results in corresponding longitudinal movement of their respective needles 216a, 216b, thereby permitting the first and second needles 216a, 216b to extend from and retract into the first and second needle lumens 218a, 218b via first and second needle ports 222a, 222b. Those skilled in the art will appreciate that the first and second needles 216a, 216b may be capable of individual and/or simultaneous movement.

A guidewire lumen 224 configured to receive a guidewire 226 or similar guide line therein may be positioned in the suture deployment device 200, and may pass the length of the device (in a so-called over-the-wire configuration) or may pass only through a portion of the distal end and exit through a side just proximal of the distal end (in a so-called rapid-exchange configuration).

As depicted in FIGS. 13B-13C, first and second needle-receiving ports 228a, 228b may be positioned within or proximate the vacuum port 210 and co-aligned with and opposing the first and second needle ports 222a, 222b, respectively. The first needle-receiving port 228a is in communication with the first suture lumen 230a and contains a first needle catch 232a attached to the first suture portion 234a that passes into the first suture lumen 230a. Similarly, the second needle-receiving port 228b is in communication with the second suture lumen 230b and contains a second needle catch 232b attached to the second suture portion 234b that passes into the second suture lumen 230b.

Depending on the particular application, the first and second suture portions 234a, 234b may be entirely separate suture lines, or may comprise opposing portions of a single common suture line that forms a loop between the first needle catch 232a and the second needle catch 232b. If the first and second suture portions 234a, 234b are part of a single common suture line, the first and second needle-receiving ports 228a, 228b may form a single opening, and the first and second suture lumens 230a, 230b may form a single lumen, in order to permit the single common suture line loop to exit freely from the suture deploying device 200.

Figure 14B:
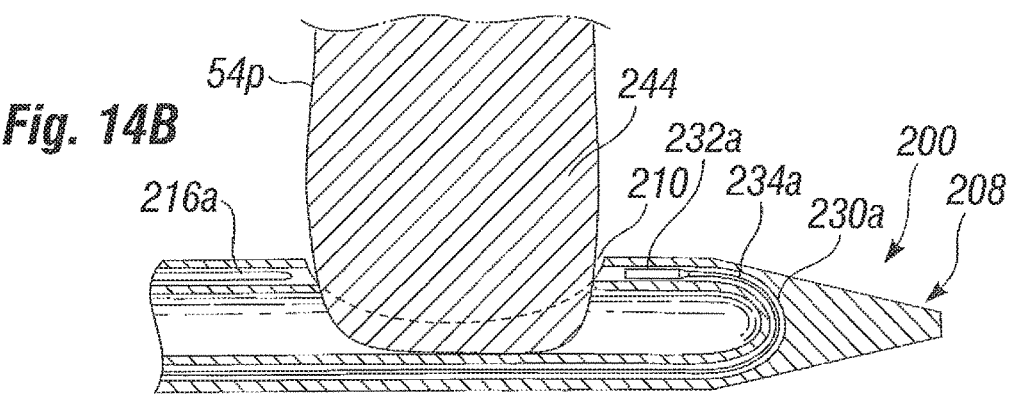
FIGS. 14B-14D are side views, in cross section, of the distal end of the suture deployment device of FIG. 14A deploying a suture through valve leaflet tissue.

FIGS. 14A-D depict a method of using the suture deployment device 200 of FIGS. 13A-13C to deploy suture line through a valve leaflet to create a replacement chordae tendinae. In FIG. 14A, the suture deployment device 200 is introduced into a patient's body until the distal end 208 is advanced into the heart 12, and more specifically (in the particular embodiment depicted) to a position where the vacuum port 210 is adjacent the posterior mitral valve leaflet 54p, in which one of the several chordae 58 has ruptured into two separate pieces 58a, 58b.

In the particular embodiment depicted in FIG. 14A, the suture deployment device 200 has been advanced percutaneously in a trans-septal approach, using a guide catheter 240, via the inferior vena cava 32 and right atrium 14 and through an opening 242 in the atrial septum 24 (or through a patent foramen ovale, not shown) into the left atrium 18 to the desired position adjacent the valve leaflet 54p, which in the particular embodiment depicted is a posterior leaflet of the mitral valve 50. Note, however, that other approaches are also within the scope of the invention, including other percutaneous and minimally invasive approaches, such as approaches via the aorta, superior vena cava, or directly through the outer heart wall, etc. Note also that the same procedure may be used for attachment to an anterior leaflet of the mitral valve.

Figure 14C:
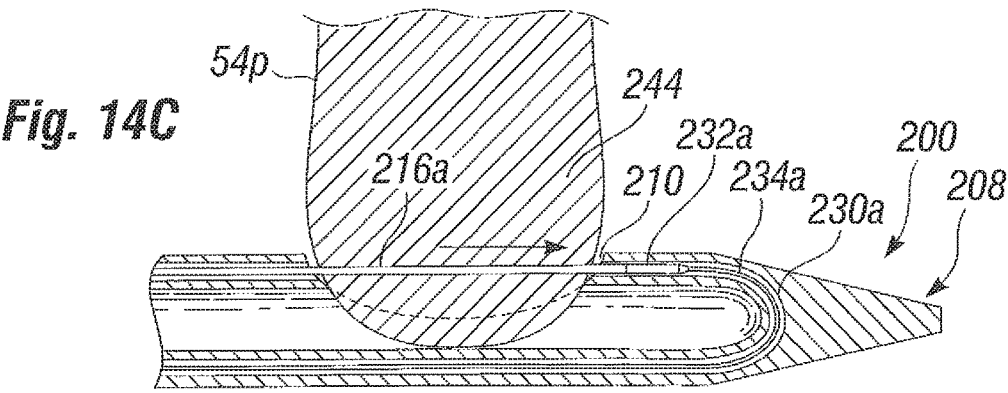
Figure 14D:
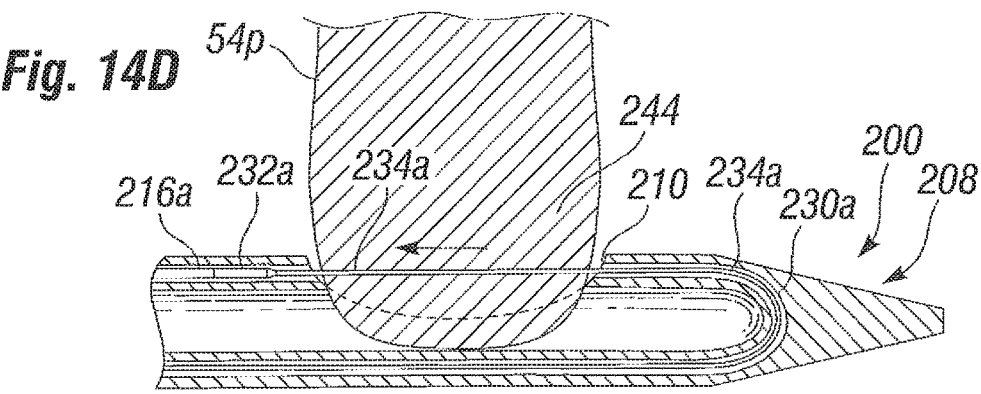

In FIG. 14B, the suture deployment device 200 uses the vacuum port 210 to grasp the valve leaflet 54p. With the valve leaflet 54p firmly held by the vacuum port 210, the suture deployment device 200 advances a needle 216a through the valve leaflet tissue 244, with the needle 216a engaging against and becoming secured to a needle catcher 232a on the far side of the valve leaflet tissue 244 and vacuum port 210, as depicted in FIG. 14C. The needle 232a is then withdrawn back through the valve leaflet tissue 244, thus dragging the needle catcher 232a and attached suture line portion 234a back through the valve leaflet tissue 244, as depicted in FIG. 14D. The device distal end 208 is then moved away from the valve leaflet 54p, with the suture line portion 234a trailing out of the device 200, as depicted in FIG. 14E.

Similar devices to that depicted and described with respect to FIGS. 14A-14E are depicted and described in pending U.S. patent application Ser. No. 10/389,721, filed on Mar. 14, 2003 and entitled "Mitral Valve Repair System and Method for Use," the entire contents of which are hereby incorporated by reference.

Figure 15:
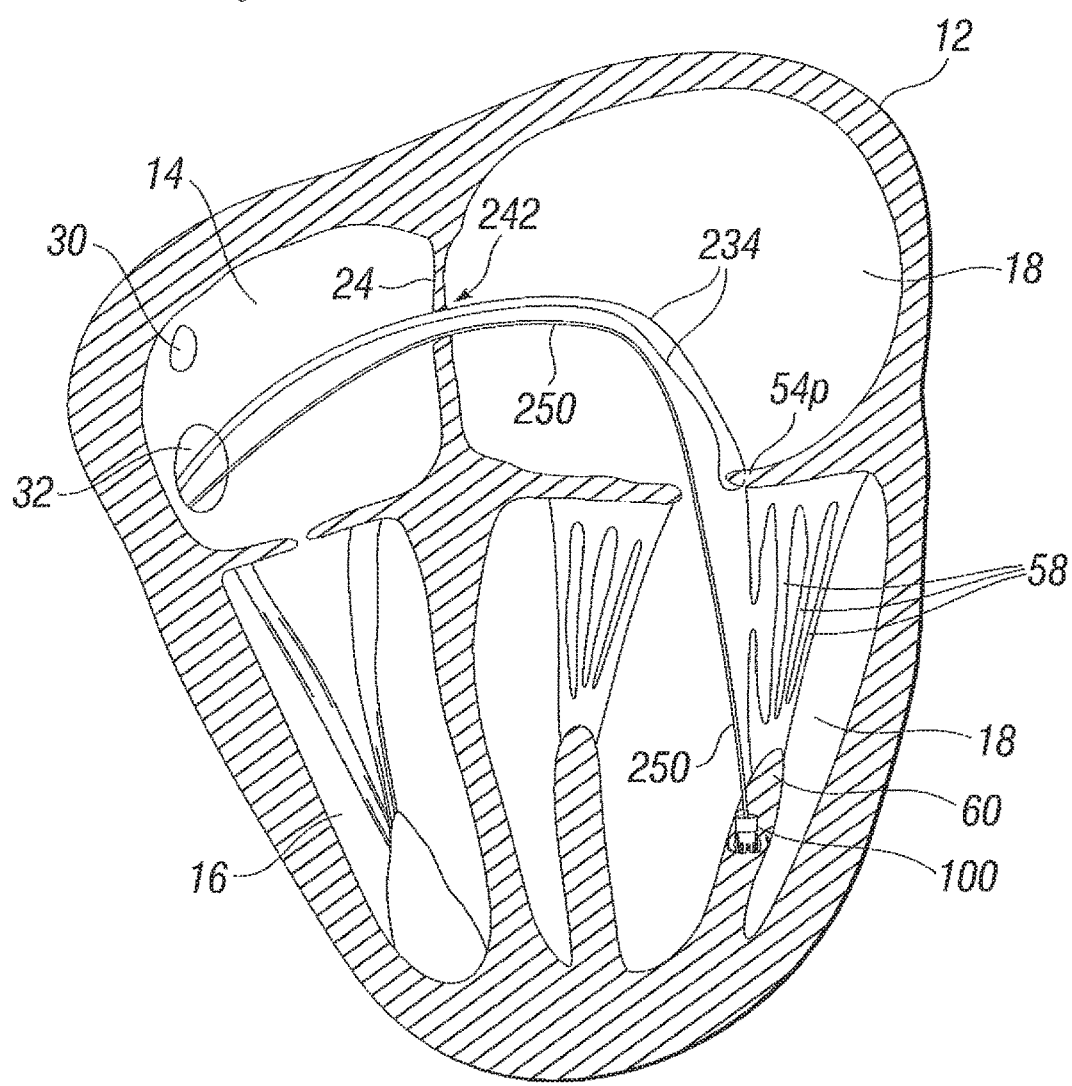
FIG. 15 is a front view of a heart, in cross section, with a suture, anchor, and elongate member deployed therein according to an embodiment of the invention.

FIG. 15 depicts an embodiment wherein an anchor 100 has previously been deployed in a papillary muscle 60 (e.g., using devices and methods such as those previously described with respect to FIG. 11, etc.), with an elongate member portion in the form of a papillary-anchored suture line 250 passing from the anchor 100 and out of the patient via the left atrium 18, atrial septum 24, right atrium 14, and inferior vena cava 32, i.e., along the same path through which the suture deployment device 200 was advanced in FIGS. 14A-14E. In such an embodiment, the previously-deployed papillary-anchored suture line 250 can actually serve as a guide line over which the suture deployment device 200 can be advanced similar to the technique of FIGS. 14A-14E, but with the papillary-anchored suture line 250 serving as a guide line there may be no need for a guide catheter 240 such as that depicted in FIGS. 14A and 14E.

With a previously-deployed anchor 100 and papillary-anchored suture line 250 already in place as in FIG. 15, the suture deployment device 200 can, after having passed a leaflet-secured suture line 234 through a valve leaflet 54p, be withdrawn from the patient as shown, with the leaflet-secured suture line 234 trailing out of the suture deployment device 200 and eventually out of the patient once the suture deployment device is completely withdrawn from the patient.

In FIGS. 16A-16D, an embodiment of a suture securing and cutting device 260 is depicted. The fastener catheter 260 has a generally tubular main body 262, a proximal end 264, and a distal end 266. The proximal end 264 includes a handle knob 268. The distal end 266 includes a suture clip 270 positioned thereon. The fastener catheter 260 may be manufactured in a variety of shapes, sizes, lengths, widths, and biologically-compatible materials as desired for a particular application.

The generally tubular main body 262 has a longitudinal inner lumen 272 therethrough which terminates in a distal opening 274. A longitudinally slidable inner body 276 is slidably positioned within the main body 262. The inner body 276 includes an inner tubular member distal end 278 which extends out of the main body distal opening 274. The inner tubular member distal end 278 itself includes an inner tubular member distal opening 280, which leads to an inner body lumen 282. These and other features are depicted in additional detail in FIGS. 16B-16D, which illustrate (in exploded fashion in FIGS. 16B-16C, and assembled in FIG. 16D), distal portions of the fastener catheter 260.

The inner body 276 includes a suture recess 284 formed in the side thereof, which in turn is in communication with the inner body lumen 282. Inner body 276 also includes a pin 286 extending radially outward therefrom. The main body 262 has a cutting recess 288 formed in an axial side thereof and a cutting member 290 which, in the embodiment depicted, is on a proximal edge of cutting recess 288. A pin recess in the form of a slot 292 extends parallel to the axis of the main body 262 and radially through to main body lumen 272. The slot 292 is thus configured to receive pin 286 in sliding relation.

In FIG. 16D, the inner body 276 is slidably positioned within main body 262, such that suture recess 284 is in alignment with cutting recess 288. Pin 286 is in slidable communication with slot 292 thereby permitting relative linear motion, but preventing relative rotational motion, between inner body 276 and main body 262. A clip 270 is positioned on the inner body distal end 278, which protrudes from the main body distal opening 274. The clip 270 includes a clip distal opening 294, clip proximal opening 296, and engagement members 298. As depicted in FIG. 16D, the clip 270 has been placed on inner member distal end 278 by deflecting the engagement members 298 radially outward until they can be placed around the outer circumference of inner body distal end 278. Accordingly, the clip 270 is secured to the inner body distal end 278 by means of the frictional engagement between the engagement members 298 and the outer surface of inner body distal end 278. Suture 234 extends through the fastener clip 270, with suture leads 234a and 234b extending through the clip distal opening 294, engagement members 298, and proximal opening 296, passing through inner member distal opening 280 and inner member lumen 282, exiting the inner member 276 via suture recess 284, and exiting the side of main body 262 through cutting recess 288.

Once the clip 270 is advanced to a desired position on the suture line 234, the inner member 276 can be retracted with respect to the main body member 262, thereby causing the inner body distal end 278 to be pulled inside the main body member 262. The clip 270 will thus be pushed off of the inner body distal end 278 by the main body 262, at which point the clip engagement members 298 move inwardly to block the clip proximal opening 296 and thereby lock the clip 270 onto the suture 234. The retraction of the inner member 276 with respect to the main body member 262 also causes the suture portions 234*a*, 234*b* to be pinched between the inner member opening 284 and the cutting member 190, so that the suture portions 234*a*, 234*b* are cut by the cutting member 290.

Similar devices to that depicted and described with respect to FIGS. 16A-16D are depicted and described in pending U.S. patent application Ser. No. 10/389,721, filed on Mar. 14, 2003 and entitled "Mitral Valve Repair System and Method for Use"; pending U.S. patent application Ser. No. 11/174,397, filed on Jun. 30, 2005 and entitled "System, Apparatus, and Method for Fastening Tissue"; pending U.S. patent application Ser. No. 11/345,208, filed on Jan. 31, 2006 and entitled "System, Apparatus, and Method for Fastening Tissue"; and pending U.S. patent application Ser. No. 11/746,009, filed on May 8, 2007 and entitled "Suture-Fastening Clip"; the entire contents of each of which are hereby incorporated by reference.

Figure 17A:
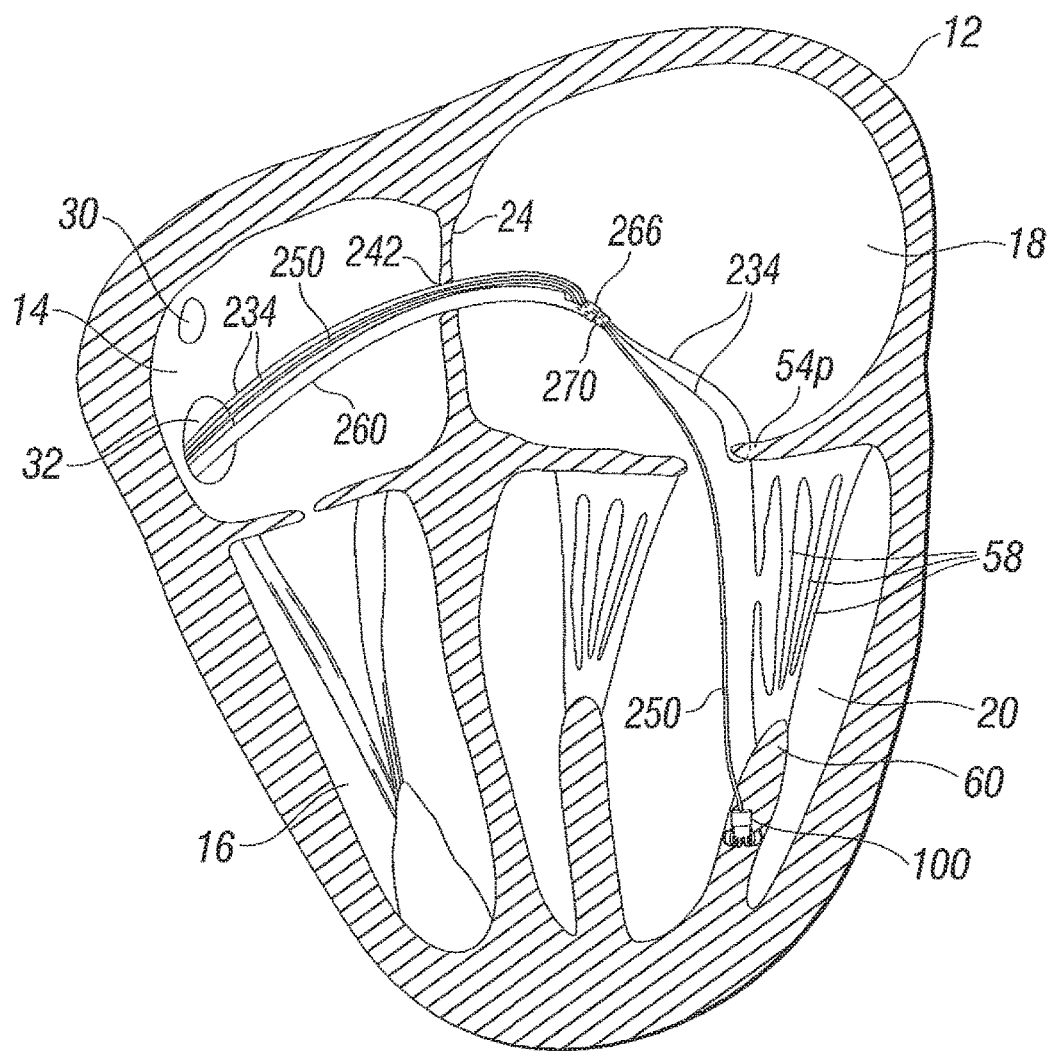
FIGS. 17A and 17B are front views of a heart, in cross section, with a suture securing and cutting catheter advancing a suture clip along suture lines and an elongate member to form a replacement chordae tendinae according to an embodiment of the invention.
Figure 17B:
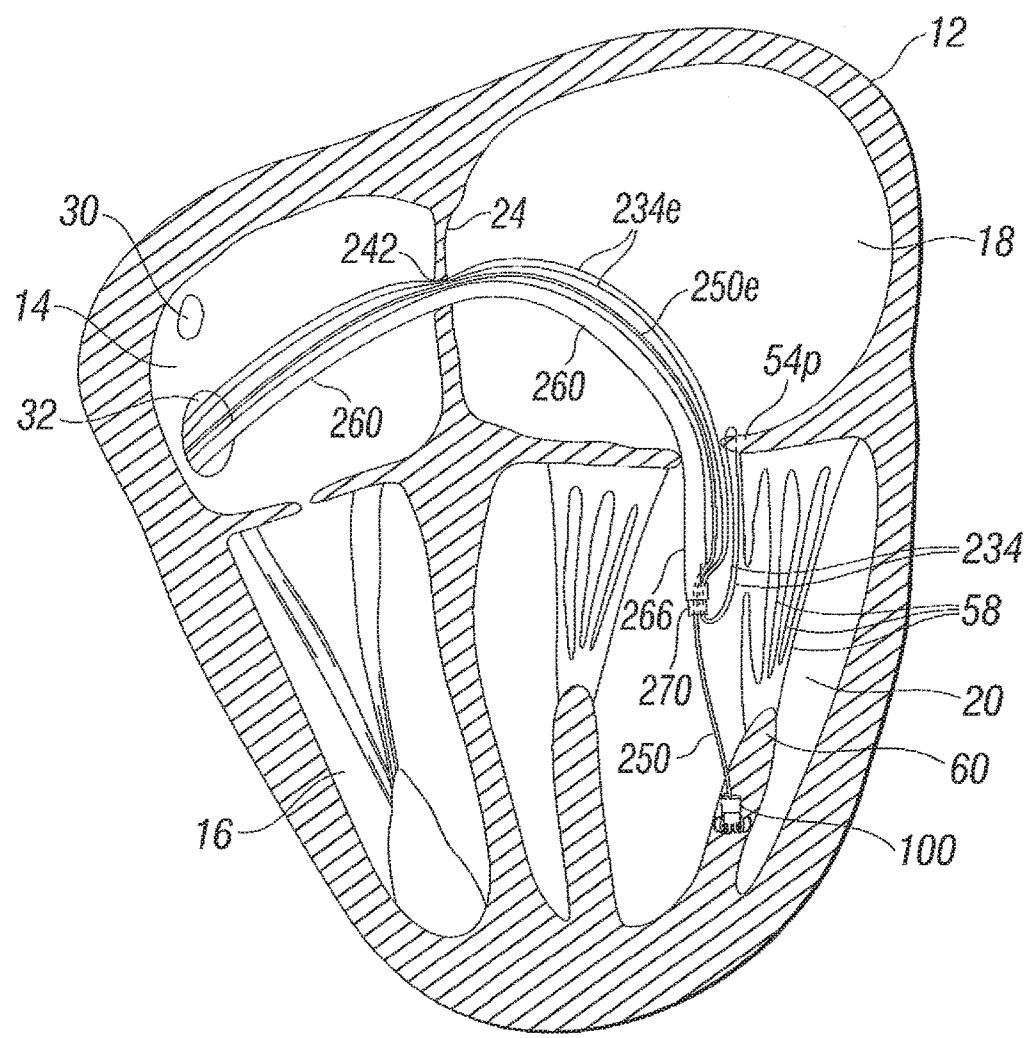
Figure 17C:
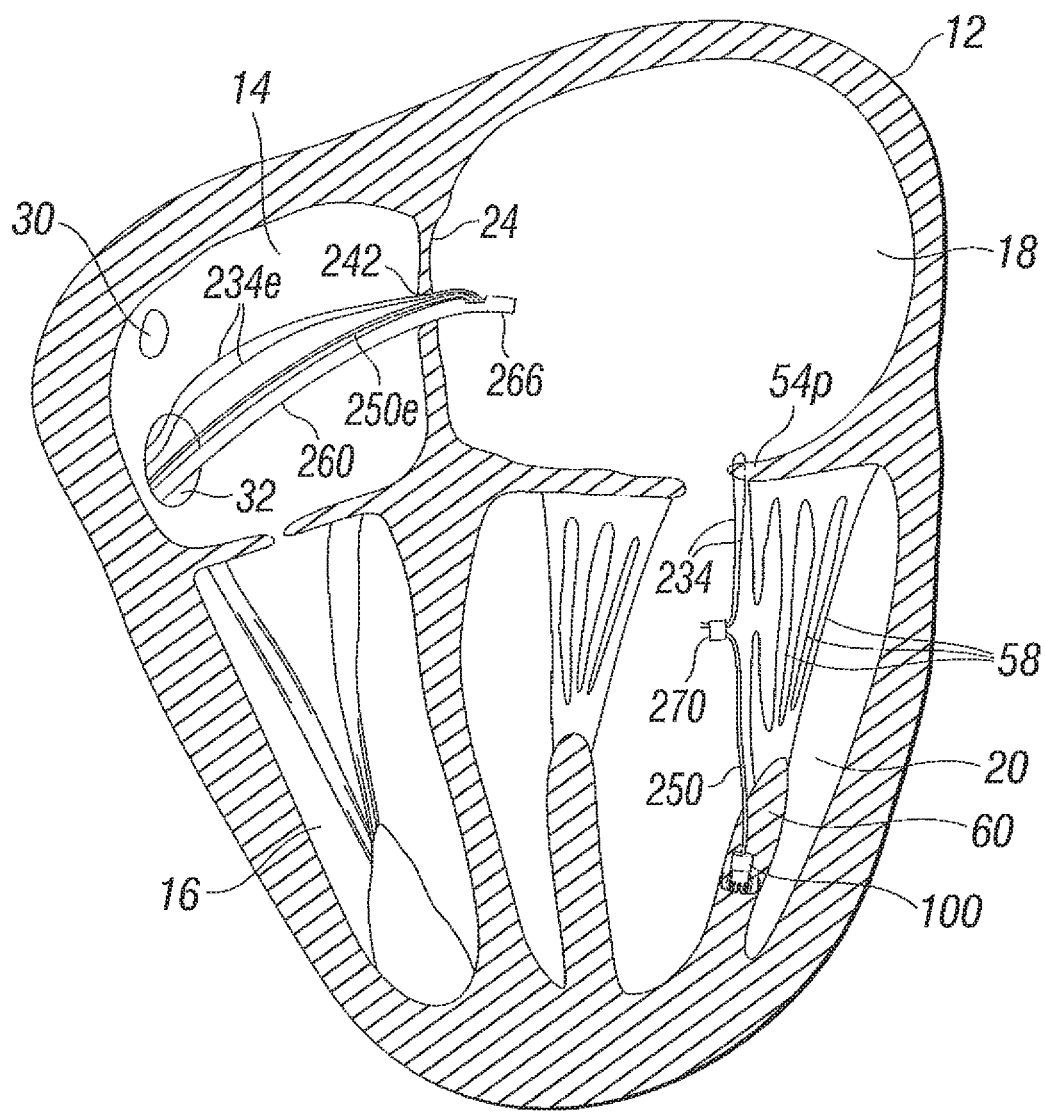
FIG. 17C is a front view of the heart of FIGS. 17A-17B with the suture clip deployed and excess suture removed to form a replacement chordae tendinae according to an embodiment of the invention.

FIGS. 17A-17C depict a method of securing the deployed suture lines 234, 250 together at a desired length in order to create a replacement chordae tendinae. In FIG. 17A, the suture securing and cutting device 260 is shown with the distal end 266 being advanced along the previously-deployed suture lines 234, 250, with the papillary-anchored suture line 250 serving to guide the suture securing and cutting device 260 into the patient's heart 12 and left ventricle 20. As the suture securing and cutting device 260 is advanced along the previously-deployed papillary-anchored suture line 250, the user (such as a surgeon or cardiologist) pulls on the proximal end of the papillary-anchored suture line 250 (which is positioned outside of the patient) to maintain slight tension as the suture securing and cutting device 260 is advanced into the left ventricle 20. The user may also pull on the proximal ends of the leaflet-secured suture line 234 to prevent it from being pushed into the patient as the suture securing and cutting device is advanced.

In FIG. 17B, the suture securing and cutting device distal end 266, with suture securing clip 270 thereon, is depicted advanced to a desired location in the left ventricle. The user pulls on the papillary-anchored suture line 250 and/or on the leaflet-secured suture line 234 to achieve a replacement chordae tendinae of a desired length. While adjusting the length of the replacement chordae tendinae, the user can monitor the heart function using various devices known in the art, such as fluoroscopy, radiography, ultrasound, etc. In one example, the user can verify the effectiveness of the replacement chordae tendinae length by monitoring blood flow using radiopaque dyes combined with fluoroscopy or by means of ultrasound. When the user sees via the heart function monitoring system(s) that the heart valve is functioning as desired, the user then knows that the replacement chordae tendinae (formed by the sutures 234, 250) is at the appropriate length. The user can then activate the suture securing and cutting device 266 to release the suture clip 270 so that it secures the sutures 234, 250 at the desired position, thereby forming the desired replacement chordae tendinae. The user also activates the suture securing and cutting device 266 to cut the excess suture portions away adjacent the clip 270.

FIG. 17C depicts the clip 270 deployed and the excess portions 234*e*, 250*e* (i.e., portions proximal of the clip 270) of the suture lines 234, 250 having been cut. The suture securing and cutting device 266 is being withdrawn from the patient, along with the excess cut-off suture portions 234*e*, 250*e*. The deployed suture lines 234, 250 are held firmly by the clip 270 to serve as a replacement chordae tendinae.

In a further embodiment of the invention, the suture deployment device 200 can be used to secure the suture line 234 directly to the papillary muscle or other heart tissue, and/or to a previously-deployed anchor. For example, in one such embodiment the suture deployment device is used to deploy the suture line 234 through the papillary muscle 60, as depicted and described with respect to FIGS. 18A-B.

Figure 18A:
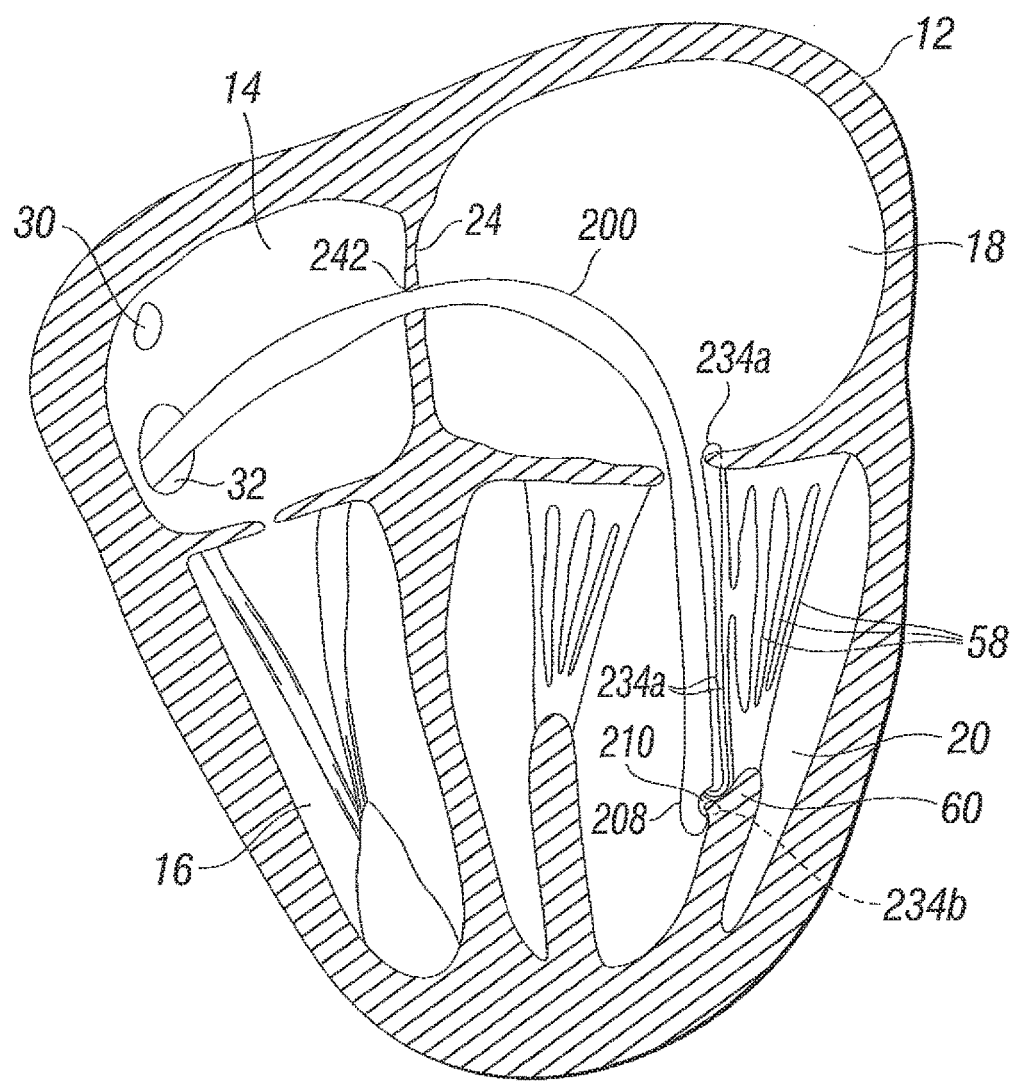

FIG. 18A depicts the suture deployment device 200 having already passed a one portion of suture line 234*a* through a valve leaflet 54*p* (as was depicted in FIGS. 14A-14E), and then being maneuvered so that the distal end 208 and vacuum port 210 positioned adjacent a papillary muscle 60 and the vacuum activated, so that the papillary muscle 60 has been grasped and held by the vacuum port 210. As the suture deployment device distal end 208 is moved from its previous position adjacent the valve leaflet 54*p* (i.e., the position depicted in FIGS. 14A-D), the leaflet-secured suture line 234*a* plays out from the suture deployment device 200. A needle from the suture deployment device is used to pass a second suture line 234*b* through the papillary muscle 60, using an apparatus and technique such as that depicted in FIGS. 14B-14D that was used to pass the leaflet-secured suture line 234*a* through the leaflet 54*p*. For example, using a device such as that depicted in FIGS. 13A-13C, needle 216*a* could be used to pass the leaflet-secured suture line 234*a* through the leaflet 54*p*, while needle 216*b* could be used to pass the papillary-secured suture line 234*b* through a portion of the papillary muscle 60.

Once the papillary-secured suture line 234*b* is secured to the papillary muscle 60, the vacuum can be discontinued so that the papillary muscle 60 is released from the vacuum port 210. As depicted in FIG. 18B, the suture deployment device 200 can then be withdrawn from the patient's heart 12, with the papillary-secured suture line 234*b* and leaflet-secured suture line 234*a* trailing out from the suture deployment device distal end 208 and eventually trailing out of the patient as the suture deployment device 200 is completely withdrawn. A suture clip can then be advanced over the suture line portions 234*a*, 234*b* and secured at a desired place thereon to create a replacement chordae of the desired length, using devices and methods such as those depicted in FIGS. 16 and 17A-17C.

Note that the deployment devices and methods depicted and described above can be varied and still fall within the scope of the invention. For example, the leaflet-secured suture line(s) can be secured to the leaflet before, after, or simultaneously with deployment of the papillary-secured suture line(s). The suture deployment device could be used to secure a papillary-secured suture line or lines directly to the papillary muscle, or to an anchor or other device deployed in the papillary muscle. For example, the suture deployment device may have a magnet near its distal end to assist in guiding the suture deployment device to an anchor that has a magnet. Also note that the suture deploying method and device can vary. For example, the suture deploying device could be configured to drive a pledget, barb-like device, or similar structure into the leaflet, papillary muscle, and/or anchor, with a suture line being secured to the pledget, barb-like device, or similar structure. The anchor, suture clip, suture lines, suture deployment device, and/or suture securing/cutting device may include one or more visualization references. For example, visualization references in the form of radiopaque marker bands may be positioned on or adjacent the distal end of the suture deployment device and/or suture securing/cutting device, and/or on the anchor, etc. The radiopaque marker bands are viewable under a fluoroscope, so that a surgeon or other user can use a fluoroscope to visualize the positions of the devices and anchors within the patient and with respect to any devices present, such as guidewires, etc. Depending on the particular application, the visualization markers on a particular device may be identical or may be different from each other. Radiopaque marker bands or other visualization references that provide different radiopaque or other visualization signatures permit a user to differentiate between particular elements (e.g., between an anchor and a suture deployment device, etc.). The efficacy of an implant (or implants) and its deployed position can be confirmed and monitored at various times during and after the deployment procedure via various techniques, including visualization methods such as fluoroscopy.

Various materials could be used to form the devices of the invention, including the anchors, suture lines, suture deployment devices, and other system components.

ANIMAL EXPERIMENTS: Two sixty kilograms adult sheep were sedated, anesthetized and connected to mechanical ventilation. A tracheal tube was inserted and the sheep put on the right side on an operating table. Under sterile conditions the chest was opened under the 5$^{th}$ rib and the pericardium was opened. A purse-string suture with a tourniquet was put on the left atrial appendage. A device of the type described above was inserted through the purse-string suture and advanced to the apex of the left ventricle. At this location, the anchor was deployed. Four weeks after the procedure, the sheep were taken back to the animal facility, anesthetized, and sacrificed by means of high dose potassium. The hearts were extracted and inspected. The anchors were found not to have penetrated the left ventricular wall and had remained in the position where they were placed during surgery. At gross inspection the anchors had healed smoothly in normal thin scar tissue and were covered by a thin layer of endothelium. A pull test was performed by pulling in the thread. At a pulling force of 1.6 Kilogram, the anchor tore out the scar tissue with surrounding heart muscle while still being intact inside the chunk of muscle. Thus one could conclude that the healing in into the left ventricular wall was stronger than the muscle itself. Using a third sheep of sixty kilograms, the same surgical procedure was performed. This time the animal was sacrificed immediately and the heart extracted. A pulling test now revealed a fixation force corresponding to a traction of 800 grams before the arms of the anchor bent back and slid out of the still intact muscle. The 800 gram fixation force is redundant to what is needed for strength when attaching a chordae tendinae to a papillary muscle and more than sufficient for treating a dilated ventricular wall.

Although the invention has been described in terms of particular embodiments and applications, one of ordinary skill in the art, in light of this teaching, can generate additional embodiments and modifications without departing from the spirit of or exceeding the scope of the claimed invention. For example, although the above devices and methods are described for use in a particular manner, the devices and methods described herein could be used in a variety of different methods of use, such as, for example, via open heart surgical access, via a beating heart surgical access (e.g., a trans-apical approach) and via a percutaneous approach. As a further example, it will be recognized that the embodiments described above and aspects thereof may also be used to treat a tricuspid valve or other valves in substantially similar manner. In addition, many modifications may be made to adapt a particular situation or device to the teachings of the invention without departing from the essential scope thereof. Furthermore, the devices and methods could be used for entirely other purposes wherein it may be advantageous to attach a suture to tissue with an anchor rather than using a needle and thread. Examples of such procedures include wound closure and treating organ prolapse. Furthermore, if desired, the anchor and/or thread may be configured to be resorbable such that they dissolve within the body over time. Accordingly, it is to be understood that the drawings and descriptions of specific embodiments herein are proffered by way of example to facilitate comprehension of the invention, and should not be construed to limit the scope thereof.

What is claimed is:

1. A method for treating a heart in a patient, the method comprising:

advancing a distal end portion of a delivery catheter to a position adjacent heart tissue at a first location, wherein the distal end portion comprises a distal end sheath having an anchor therein, wherein the anchor is configured to radially expand from a delivery configuration to a tissue-engaging configuration, wherein the anchor comprises a central body having a central lumen and a plurality of radially extendable elements positioned around a circumference of a distal end of the central body, wherein in the delivery configuration the radially extendable elements are radially retracted, and wherein in the tissue-engaging configuration the radially expandable elements are radially extended away from the central body, wherein during advancing of the distal end portion the radially extendable elements are in the delivery configuration within the distal end sheath;

deploying the anchor into contact with heart tissue at the first location and transforming the anchor from the delivery configuration to the tissue-engaging configuration, wherein the radially extendable elements radially extend away from the central body into contact with the heart tissue at the first location;

passing an elongate member from the first location, across a heart chamber, and through a heart wall, wherein a first end of the elongate member is secured to the anchor;

securing a clip to heart tissue at a second location at an apex of the heart, wherein the clip is configured to slidingly receive the elongate member and to lock onto the elongate member to prevent sliding movement by the elongate member with respect to the clip, wherein the second location is on the opposite side of the heart wall from the first location, wherein the elongate member is slidingly received within the clip;

adjusting the length of the elongate member between the anchor and the clip by sliding the elongate member within the clip so that the elongate member extends across the heart chamber and provides tension between the anchor and the clip;

locking the clip to the elongate member to prevent sliding movement between the clip and the elongate member; and removing the delivery catheter from the patient.

2. The method of claim 1, wherein the radially extendable elements have sharp points at distal ends of the radially extendable elements, and wherein deploying the anchor comprises passing the sharp points into the tissue at the first location.

3. The method of claim 1, wherein the first location is in an exterior heart wall.

4. The method of claim 1, wherein the heart chamber is a left ventricle.

5. The method of claim 4, wherein the clip is positioned on the outside of the heart wall at the apex.

6. The method of claim 5, wherein the anchor and the elongate member are implanted in the patient via a transapical approach.

7. A method of improving heart function in a human heart, the method comprising:

advancing an elongate tensioning element and a radially-expandable device into a ventricle of a human heart via a catheter using a transapical approach, wherein the radially-expandable device is secured to a distal end of the elongate tensioning element, wherein the radially-expandable device includes radially-extendable elements, wherein the radially-extendable elements are held in a radially restrained condition;

deploying the radially-expandable device at a first location within the human heart by extending the radially-extendable elements radially outward to engage the device with heart tissue at the first location;

selectively tensioning the elongate tensioning element within the heart by pulling on a proximal portion of the elongate tensioning element extending outside of the heart wall via an opening at the heart apex; and placing a locking clip against an outside surface of the heart at the heart apex with the elongate tensioning element locked in the locking clip to hold the elongate tensioning element in a desired level of tension between the locking clip and the radially-expandable device.

8. The method of claim 7, wherein extending the radially extendable elements radially outward includes ejecting the radially-expandable device out of the distal end of the catheter.

9. The method of claim 7, wherein the radially-extendable elements include prongs with sharp ends, and wherein engaging the device with heart tissue at the first location includes passing the sharp ends into the tissue at the first location.

10. The method of claim 7, wherein the surface of the radially-extendable elements is configured to promote tissue ingrowth.

11. The method of claim 7, wherein the first location is at a wall of the ventricle.

12. The method of claim 7, further comprising:

actively monitoring heart function to confirm that proper tension is applied by the elongate tensioning element between the radially-expandable device and the locking clip.

13. The method of claim 7, further comprising:

after placing the locking clip against an outside surface of the heart, cutting excess portions of the elongate tensioning element that extend proximally from the locking clip.

14. A method of repairing heart function, the method comprising:

advancing a distal end of a catheter into a heart of a patient via a transapical approach, wherein the distal end comprises a distal opening, wherein an expandable device is positioned within the distal end of the catheter, wherein the expandable device is configured to be anchored to heart tissue with a plurality of radially-extendable elements movable between a delivery configuration in which the radially-extendable elements are retracted, and a deployed configuration in which the radially-extendable elements extend radially outward from the expandable device;

positioning the distal end of the catheter adjacent a first location in the heart;

extending the radially-extendable elements outwardly to engage heart tissue at the first location in the heart;

pulling on a proximal portion of an elongate member extending outside of an apex of the heart to adjust a length of the elongate member extending between the apex and the expandable device; and positioning a locking clip against an outside surface of the heart at the heart apex with the elongate member locked in the locking clip to fix the length of the elongate member extending between the apex and the expandable device.

15. The method of claim 14, wherein the first location is within a left ventricle of the heart.

16. The method of claim 14, wherein the first location is at an exterior wall of the heart.

17. The method of claim 14, further comprising:

actively monitoring heart function prior to positioning the locking clip against an outside surface of the heart at the heart apex with the elongate member locked in the locking clip.

18. The method of claim 14, wherein the radially-extendable elements includes prongs with sharp ends, and wherein deploying the expandable device includes passing the sharp ends into heart tissue at the first location.

* * * * *